(12) United States Patent
Gyermek et al.

(10) Patent No.: US 6,274,757 B1
(45) Date of Patent: Aug. 14, 2001

(54) NEUROMUSCULAR RELAXANTS

(75) Inventors: Laszlo Gyermek, Rancho Palos Verdes; Chingmuh Lee, Palos Verdes Estates; Young-Moon Cho, Los Angeles, all of CA (US)

(73) Assignee: Newlaxant LLC, Rancho Palos Verdes, CA (US)

( * ) Notice: Subject to any disclaimer, the term of this patent is extended or adjusted under 35 U.S.C. 154(b) by 0 days.

(21) Appl. No.: 09/429,998

(22) Filed: Oct. 29, 1999

Related U.S. Application Data

(63) Continuation of application No. 08/957,240, filed on Oct. 24, 1997, now Pat. No. 5,990,124.

(51) Int. Cl.$^7$ .................................................. C07L 69/76
(52) U.S. Cl. ........................... 560/84; 560/80; 560/127; 560/128; 560/190
(58) Field of Search ............................ 560/80, 84, 127, 560/128, 190

(56) References Cited

U.S. PATENT DOCUMENTS

| | | | |
|---|---|---|---|
| 2,734,062 | 2/1956 | Hotovy et al. | 546/130 |
| 2,746,964 | * 5/1956 | Biel et al. | 546/188 |
| 3,275,679 | * 9/1966 | Brotherton et al. | 560/80 |
| 5,494,898 | * 2/1996 | Cheng et al. | 514/18 |
| 5,990,124 | 11/1999 | Gyermek et al. | |

FOREIGN PATENT DOCUMENTS

| | | |
|---|---|---|
| 3727915 | 3/1958 | (CH) . |
| 572933 | 1/1976 | (CH) . |
| 1287588 | 1/1969 | (DE) . |
| 1933478 | 1/1971 | (DE) . |
| 1770183 | 9/1971 | (DE) . |
| 886183 | 1/1962 | (GB) . |
| 1398050 | 6/1975 | (GB) . |
| 142597 | 12/1951 | (HU) . |
| WO81/01710 | 6/1981 | (WO) . |
| WO96/97410 | 3/1996 | (WO) . |

OTHER PUBLICATIONS

Gyermek et al., "The Pharmacology of Tropane Compounds in Relation to their Steric Structure," *The Journal of Pharmacy and Pharmacology* 9:209–229 (1957).

Haining et al., "The Neuromuscular Blocking Properties of a Serial of Bis–Quaternary Tropeines," *Brit. J. Pharmacol.*, 15:71–81 (1960).

Nador et al., Attempts to Find New Compounds with Curare–Like Effects, Part III. Quaternary Derivatives of Dicarboxyl Tropine Esters, *Acta Chimica Hung.*, pp. 369–374 (1952).

* cited by examiner

*Primary Examiner*—Zinna Northington Davis
(74) *Attorney, Agent, or Firm*—Lyon & Lyon LLP

(57) ABSTRACT

Alkoxy and/or acyloxy disubstituted and polysubstituted aralkyl and aralkenyl bis-quaternary ammonium derivatives of cyclic alkanol diesters have neuromuscular relaxant properties.

4 Claims, 1 Drawing Sheet

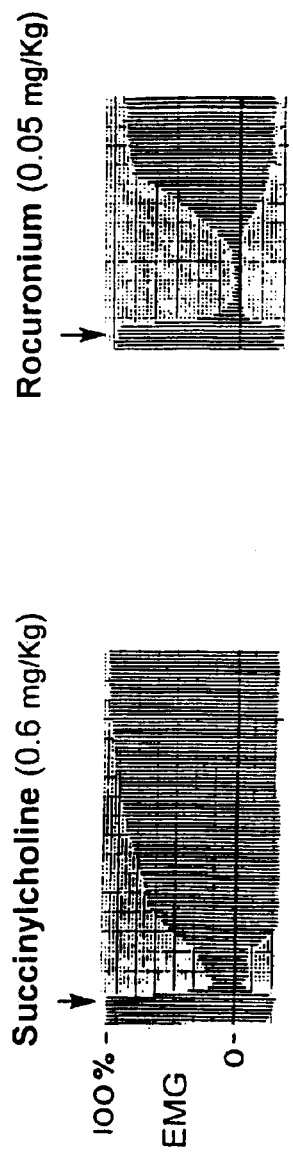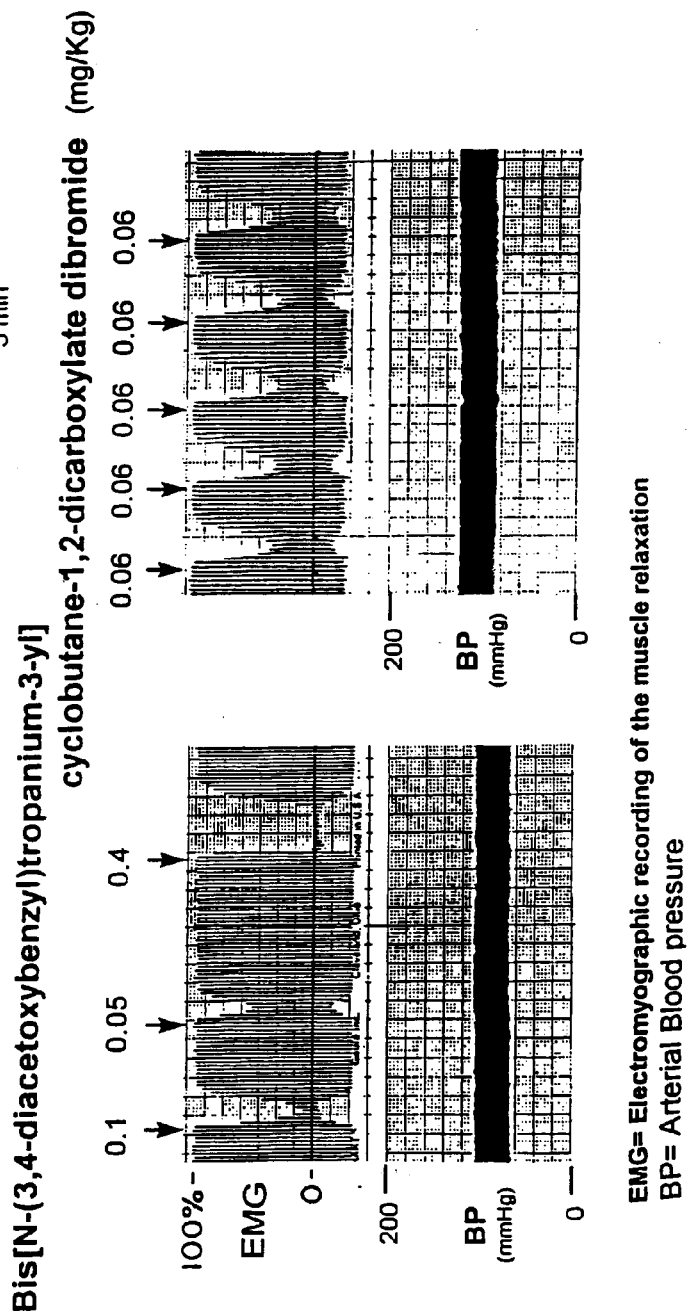

NEUROMUSCULAR RELAXANTS

This application is a continuation of application Ser. No. 08/957,240, filed Oct. 24, 1997 now U.S. Pat. No. 5,990,124.

FIELD OF INVENTION

This invention relates to compounds useful as muscle relaxants. In one of its more particular aspects, the invention relates to a series of alkoxy- and acyloxy-substituted aralkyl and aralkenyl bis quaternary ammonium derivatives of cyclic alkanol diesters. This invention also relates to methods for the preparation and use of such compounds as muscle relaxants and to pharmaceutical compositions containing such compounds.

BACKGROUND OF THE INVENTION

During surgery it is preferred that the muscles of the patient be as relaxed as possible. Although general anesthesia renders the patient unconscious, it only rarely provides sufficient skeletal muscle relaxation. A variety of muscle relaxant agents, also known as neuromuscular blocking agents, are used for muscle relaxation during surgery. One muscle relaxant used frequently in the past is succinylcholine, which has a very rapid onset and short duration of clinical action. However, succinylcholine elicits muscle membrane "depolarization" which makes this compound less desirable. Furthermore, it may produce serious side effects.

Several other so called "non-depolarizing" muscle relaxants are known and used in anesthesia and surgery. These chemically diverse non-depolarizing muscle relaxants include, among others: tubocurarine, pancuronium, atracurium, cisatracurium, vecuronium, mivacurium and rocuronium. The common structural feature of these compounds is one or usually two quaternary nitrogen atoms. They are all clinically acceptable because they produce only mild or no side effects. However, their onset of action is too slow and their duration of action is too long. Thus, these agents, without exception, fall short of the requirements of an "Ideal" surgical muscle relaxant.

Hungarian Patent No. 142,597 issued on Sep. 15, 1955, discloses a series of compounds having a pair of tropine moieties bound by an ester linkage to an aliphatic or aromatic diacid. The nitrogens on both tropines are quaternized with alkyl or unsubstituted or monosubstituted benzyl groups.

Certain naturally occurring alkaloids consist of dicarboxylic acid esters of azabicyclo alkanols, such as belladonnine, which is a bis tropinester, and thesine, which is a bis oxymethyl pyrrolizidine ester. Only the ethyl quaternary derivative of belladonnine and the methyl quaternary derivative of thesine have been reported as muscle relaxants.

Some other neuromuscular blocking agents that include pairs of quaternary nitrogens as part of a tropane ring system have been reported in the literature. In these compounds tropinyl moieties are joined by bridging the two quaternary nitrogens. U.S. Pat. No. 2,746,964 (1953) discloses dicarboxylic acid esters of 3-piperidinol and their alkyl quaternary derivatives.

It is an object of the present invention to provide new and improved muscle relaxants which are characterized by very rapid onset and short duration of neuromuscular blocking action.

SUMMARY OF THE INVENTION

In our research for the "ideal" muscle relaxant we have discovered that in general, di- or poly- alkoxy- or acyloxy- substituted aralkyl and aralkenyl quaternary ammonium derivatives of cyclic aminoalkanol diesters either exhibited less side effects such as decreased blood pressure and increased heart rate or greater potencies than other agents with alkyl, unsubstituted aralkyl, or monosubstituted aralkyl quaternary groups. In particular, such alkoxy- and acyloxy-substituted aralkyl and aralkenyl quaternary derivatives of cyclic aminoalkanol diesters were much more rapidly and shorter acting than any "nondepolarizing" muscle relaxant compound hitherto known. This discovery was entirely unexpected and unpredicted and thus forms the basis of this invention.

This invention consists of a series of di- or poly-alkoxy- or acyloxy-substituted aralkyl and aralkenyl bis-quaternary ammonium derivatives of cyclic alkanol esters of dicarboxylic acids as neuromuscular relaxants, methods of making and using them, and pharmaceutical compositions containing them.

The first aspect of this invention is a group of compounds I/a, having the general formula illustrated below:

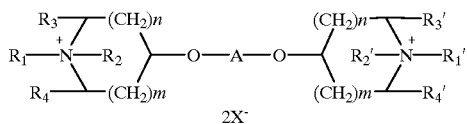

A second aspect of this invention is a group of compounds I/b, having the general formula illustrated below:

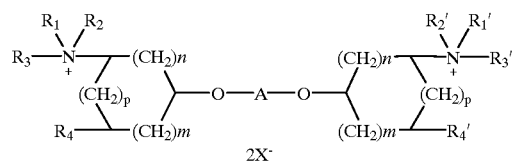

A third aspect of this invention is a group of compounds I/c, having the general formula illustrated below:

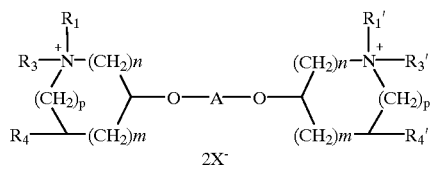

where A is alkanedicarbonyl, alkenedicarbonyl, alkynedicarbonyl, cycloalkanedicarbonyl, cycloalkenedicarbonyl, bicycloalkanedicarbonyl, bicycloalkenedicarbonyl, polycycloalkanedi-carbonyl, polycycloalkenedicarbonyl, aromatic dicarbonyl, substituted alkanedicarbonyl, substituted alkenedicarbonyl, substituted alkynedicarbonyl, substituted bicycloalkanedicarbonyl, substituted bicycloalkenedicarbonyl, or substituted aromatic dicarbonyl; $R_I$ and $R_I'$ are di- or polysubstituted aralkyl or aralkenyl in which at least one of the substituents is alkoxy or acyloxy; $R_2$ and $R_2'$ are alkyl or alkenyl; n is 0, 1, or 2; m is 0, 1, or 2; p is 0, 1, or 2; $R_3$ and $R_3'$ are H, $CH_3$, or lower alkyl; $R_4$ and $R_4'$ are H, $CH_3$, or lower alkyl; $R_3$ and $R_4$ can also be $-(CH_2)_g-$, $-CH=CH-$, $-(CH_2)_h-O-(CH_2)_k-$, $-$epoxy$-$, or $-(CH_2)_h-S-(CH_2)_k-$, where g is 2, 3, 4, or 5, h is 1 or 2, and k is 1 or 2; and $R_3'$ and $R_4'$ can also be $-(CH_2)_g-$, $-CH=CH-$, $-(CH_2)_h-O-(CH_2)_k-$,

or —(CH$_2$)$_h$—S—(CH$_2$)$_k$—, where g is 2, 3, 4, or 5, h is 1 or 2, and k is 1 or 2; X is a pharmaceutically acceptable anion; R$_1$ and R$_1$' can be the same or different; likewise R$_2$ and R$_2$', R$_3$ and R$_3$', and R$_4$ and R$_4$' can be the same or different.

A fourth aspect of this invention is the method of use of the compounds of the general formulae 1/a–1/c as neuromuscular relaxants.

A fifth aspect of this invention is a pharmaceutical composition, including the compounds of general formulae 1/a–1/c and a pharmaceutically acceptable excipient.

DESCRIPTION OF THE PREFERRED EMBODIMENTS

Definitions

As used herein, the term "alkyl" refers to a hydrocarbon radical having from 1 to 20 carbon atoms. In this invention alkyl can be non-substituted, for example, methyl, butyl, octyl, and dodecyl.

As used herein, the term "alkenyl" refers to any hydrocarbon radicals having from 1 to 20 carbon atoms that includes at least one carbon-carbon double bond at any position. Examples include ethenyl, 2-butenyl, 5-octenyl, and 2, 10-dodecenyl.

As used herein, the term "alkynyl" refers to hydrocarbon radicals having from 1 to 20 carbon atoms that includes at least one carbon-carbon triple bond at any position. Examples include acetylenyl, 2-butynyl, 5-octynyl, and 1,7-decanediynyl.

As used herein, the term "aryl" refers to aromatic hydrocarbon radicals. Examples include phenyl, naphthyl, and anthracyl.

As used herein, the term "aralkyl" refers to aryl hydrocarbon radicals including an alkyl portion as defined above. Examples include benzyl, phenylethyl, and 6-napthylhexyl.

As used herein, the term "aralkenyl" refers to aryl hydrocarbon radicals including an alkenyl portion, as defined above. Examples include styryl, 3-benzylpropenyl, and 6-naphthyl-2-hexenyl.

As used herein, the term "cycloalkyl" refers to an alkyl that has its carbon atoms arranged into a ring. Examples include cyclohexyl, cyclobutyl, and cyclododecyl.

As used herein, the term "cycloalkenyl" refers to an alkenyl that has its carbon atoms arranged into a ring. Examples include cyclohexenyl and 1,5-cyclododecadienyl.

As used herein, the term "bicycloalkyl" refers to an alkyl that has its carbon atoms arranged into two rings. Examples include decahydronaphthyl, norbornyl, and bicyclo [2.2.2] octyl.

As used herein, the term "bicycloalkenyl" refers to an alkenyl that has its carbon atoms arranged into two rings. Examples include norbornenyl and 1,2,3,4,5,6,7,8-octahydronaphthyl.

As used herein, the term "polycycloalkyl" refers to an alkyl that has its carbon atoms arranged into three or more rings.

As used herein, the term "polycycloalkenyl" refers to an alkenyl that has its carbon atoms arranged into three or more rings.

As used herein, the term "substituted" refers to a hydrocarbon radical selected from the groups alkyl, alkenyl, alkynyl, aryl, aralkyl, aralkenyl, cycloalkyl, cycloalkenyl, bicycloalkyl, bicycloalkenyl, polycycloalkyl, polycycloalkenyl, and all as defined above, where one or more hydrogens have been replaced with alkyl, fluoride, chloride, bromide, iodide, hydroxy, mercapto, alkoxy, acyloxy, alkylthio, arylthio, acetamido, amino, or nitro group(s). Also the term "substituted" refers to a hydrocarbon radical selected from the groups alkyl, alkenyl, alkynyl, aryl, aralkyl, aralkenyl, cycloalkyl, cycloalkenyl, bicycloalkyl, bicycloalkenyl, polycycloalkyl, polycycloalkenyl, and all as defined above, where one or more carbons have been replaced with oxygen, sulfur, nitrogen, or silicon atom(s).

In case of the quaternizing aralkyl or aralkenyl groups, "disubstituted or polysubstituted" refers to two or more substituents, one or more of which shall be alkoxy or acyloxy and the other(s) shall be one or more identical or different substituents selected from the groups: alkyl, alkenyl, aryl, aralkyl, halogen, hydroxy, mercapto, alkoxy, aryloxy, acyloxy, acetamido, amino, alkylthio, arylthio, imino or nitro groups which replace two or more hydrogen atoms of the aralkyl or aralkenyl moiety.

As used herein, the term "alkyl-cycloalkyl" refers to a hydrocarbon radical including an alkyl and a cycloalkyl group. Examples include 3-methylcyclohexyl and 4-hexylcycloheptyl.

As used herein, the term "alkanedicarbonyl" refers to a radical that includes an alkyl as defined above and two carbonyl groups. Examples include succinyl, glutaryl, sebacyl, 1,11-dicarboxyundecanyl, and the like.

As used herein, the term "alkenedicarbonyl" refers to a radical that includes at least one carbon-carbon double bond and two carbonyl groups. Examples include 1,3-dicarboxypropenyl, 1,6-dicarboxy-3-hexenyl, and traumatyl (1,10-dicarboxy-2-decenyl).

As used herein, the term "alkynedicarbonyl" refers to a radical that includes at least one carbon-carbon triple bond and two carbonyl groups. Examples include 1,2-dicarboxypropynyl, 1,6-dicarboxy-2-hexynyl, and the like.

As used herein, the term "bicycloalkanedicarbonyl" refers to a radical that includes bicycloalkenyl as defined above and two carbonyl groups. Examples include 5-norbornane-2,3-dicarbonyl, dicahydronaphthalene-1,5-dicarbonyl, and 9,10-dihydro-9,10-ethanoanthracene-11,12-dicarbonyl.

As used herein, the term "bicycloalkenedicarbonyl" refers to a radical that includes bicycloalkenyl as defined above and two carbonyl groups. Examples include 3,6-endomethylene-1,2,3,6-tetrahydrophthaloyl and 1,2,3,4,5,6,7,8-octahydronaphthalene-1,5-dicarbonyl.

As used herein, the term "aromatic dicarbonyl" refers to a radical that includes an aromatic group substituted with two carbonyl groups. Examples include phthalyl, terephthalyl, 1,4-dicarboxynaphthyl, and the like.

As used herein, the term "acyloxy" refers to RC(O)O— in which R is a normal or substituted hydrogen, alkyl, alkenyl, alkynyl, aryl, cycloalkyl, cycloalkenyl, bicycloalkyl, or bicycloalkenyl. Examples include acetoxy, propionyloxy, 2,3-difluorobutyryloxy, benzoyloxy, cyclopropylacetoxy and chloroacetoxy.

As used herein, the term "tropine" refers to tropine (8-methyl-8-azabicyclo[3.2.1]octan-3α-ol), also known as alpha or endo tropine, and pseudotropine (8-methyl-8-azabicyclo[3.2.1]octan-3β-ol), also known as beta or exo tropine, dependent on the configuration of the hydroxy group attached to the C3 atom of tropine.

As used herein, the term "granatanol" refers to 9-methyl-9-azabicyclo[3.3.1]nonan-3α-ol or 9-methyl-9-azabicyclo[3.3.1]nonan-3β-ol, and also the term "granatanine" refers to 9-methyl-9-azabicyclo[3.3.1]nonane. It will of course be realized that the nitrogen atom of tropine and of granatanol is already methyl substituted. Therefore, when the tropine or granatanol nitrogen is referred to as substituted, as in N-methyltropinium iodide, it will be understood that the nitrogen is a quaternary nitrogen and the halide is present for charge balance.

As used herein, the term "pharmaceutically acceptable anion" refers to an anion that has little or no toxic effect and does not significantly influence the pharmacological action of a pharmaceutically administered dose. Examples include chloride, bromide, iodide, nitrate, sulfate, phosphate, sulfonate, mesylate, besylate, tosylate, and the like.

A variety of optical isomers, enantiomeric pairs, and diastereomeric pairs exist for many of the compounds within the scope of the present invention. All such compounds are intended, as are all mixtures of optical isomers, enantiomeric pairs and diastereomeric pairs, for each structural variation, including all pure compounds and racemic mixtures.

Both cis and trans geometrical isomers and mixtures are intended.

Syntheses

There will now be described various synthetic pathways for preparing the compounds of the present invention. These pathways will be illustrated using N-methyl-8-azabicyclo [3.2.1]octan-3α-ol (tropine) as an example of the starting material. Other suitable cyclic aminoalkanols can be used as well.

SYNTHETIC PATHWAY A

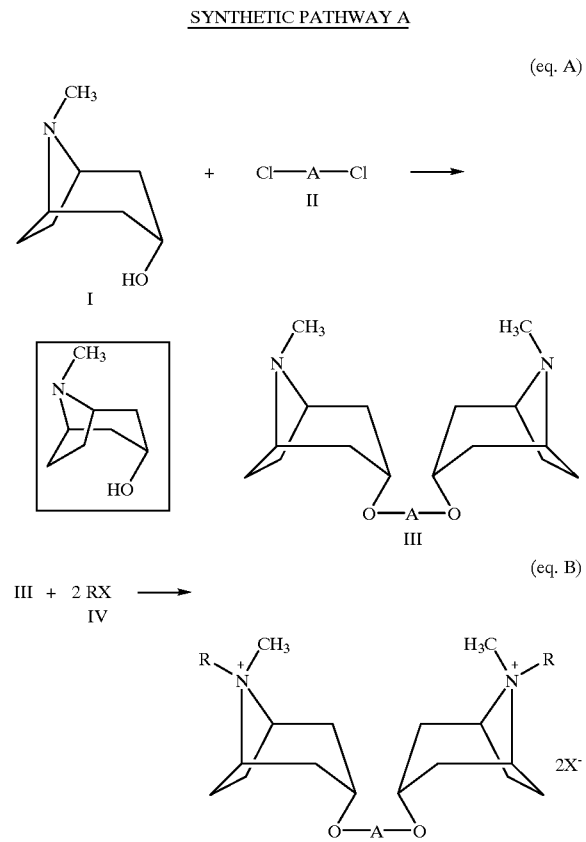

Referring to eq. A of Synthetic Pathway A, the procedure is carried out as follows. To a cooled solution of one equivalent of the appropriate diacyl halide (II) in dry methylene chloride in an ice bath is added dropwise two equivalents of tropine in dry methylene chloride, and then the mixture is allowed to warm up to room temperature. After the reaction mixture is poured into the cold water, the aqueous layer is adjusted to pH 10–11 with 6N NaOH aqueous solution, and extracted with chloroform. The diester (III) is then purified by a chromatographic technique.

In eq. B, one equivalent of the purified diester (III) is taken up in a moderately polar aprotic solvent, such as acetone or acetonitrile. Two and one-half equivalents of the appropriate alkoxy, acyloxy or alkoxyacyloxy substituted aralkyl or aralkenyl halide, RX (IV) are added. The resulting solution is heated at between 50° C. and 150° C. for 6 to 12 hours depending on the reactants. The resulting quaternary salts are filtered, and purified by recrystallization.

SYNTHETIC PATHWAY B

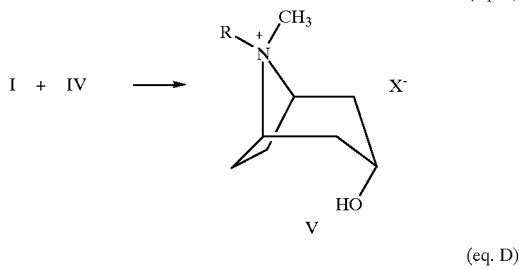

(eq. C)

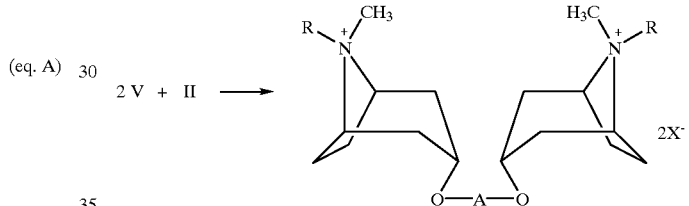

(eq. D)

Referring to eq. C of Synthetic Pathway B, in an alternative synthetic pathway one equivalent of the appropriate tropine (I) and one and one-quarter equivalents of the desired alkoxy, acyloxy or alkoxyacyloxy substituted aralkyl or aralkenyl halide (IV) are heated together in a moderately polar aprotic solvent, such as acetone or acetonitrile, for between 6 and 12 hours at between 50° C. and 100° C. The resulting quaternary ammonium salt (V) is filtered and purified by recrystallization.

Then, as shown in eq. D, two equivalents of the recrystallized quaternary salt (V) are reacted with one equivalent of the appropriate organic diacyl halide (II) in dry methylene chloride in a sealed vessel. The ingredients are heated in a closed vessel at 80–100° C. After the solvent is removed, the residue is purified by recrystallization and pure compound of Formula 1/a, 1/b and 1/c are obtained.

The compounds of Formula 1/a–1/c of this invention can also be asymmetrical diammonium esters. These compounds are made by the following method: No more than one equivalent of a first, alkoxy or acyloxy substituted aralkyl or aralkenyl halide (RX) and one equivalent of diester (III) in acetone or acetonitrile are heated at 50° C. for 12 hours; To the reaction mixture is added a second, quaternizing compound, RX (IV). Then the reaction mixture is heated again at 80–100° C. for 12 hours. The resulting precipitate is purified by recrystallization.

An alternative to synthetic pathway A is illustrated in Synthetic Pathway C.

Synthetic Pathway C

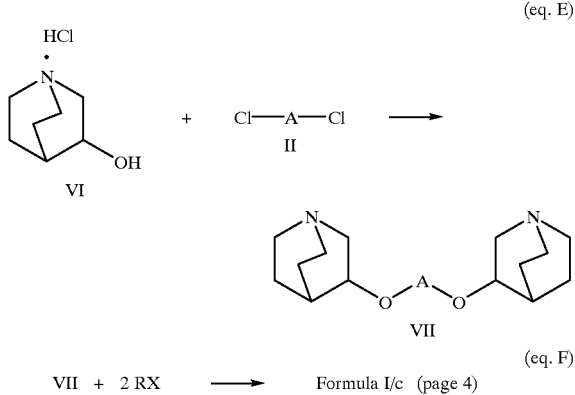

(eq. E)

VII + 2 RX → Formula I/c (page 4)     (eq. F)

Other suitable cyclic aminoalkanol hydrochlorides, such as tropine hydrochloride or granatanol hydrochloride, can be used as well.

Utility

The compounds of Formulae 1/a, 1/b and 1/c show marked activity as neuromuscular blocking agents. Such agents are typically administered intravenously. The form of administration can be a single injection, a series of injections, or the agent can be given as a component of an intravenous infusion. The compounds of this invention are characterized by rapid onset and short duration of action to the extent that they are clearly superior to any existing known muscle relaxants. Regarding side effects, the compounds of this invention have markedly reduced cardiovascular side effects associated with succinylcholine, tubocurarine or gallamine, the earlier prototypes of clinically used muscle relaxants.

The bolus dosage may vary markedly between each individual patient as it does with other muscle relaxants, but generally, as estimated on the basis of animal experiments, the dose will be between 0.1 and 1.0 mg/kg of body weight. The precise dose must be arrived at after having considered each individual case, including age, sex, weight and general condition of the patient and the degree of muscle relaxation desired.

The form of dosage can be liquid solution, either for direct injection or for addition to an intravenous fluid, or it can be a solid powder or granular material to be made into a solution prior to use. The liquid or solid can be formulated by any conventional means.

One or more pharmaceutically acceptable excipients or adjuvants may be included in a clinical formulation, including pH modifiers, stabilizers, preservatives, biologically necessary salts, sugars, and the like.

The activity of these compounds can be tested by any of several methods.

The utility of the compounds of Formulae 1/a, 1/b and 1/c have been tested by using anesthetized rats and/or cats, rabbits, dogs, guinea pigs, pigs, or monkeys. A leg tendon is attached to a transducer. An appropriate motor nerve, e.g. the sciatic or common peroneal nerve is stimulated. The resultant muscle twitches are transduced and recorded. As the neuromuscular blocking agents of this invention are administered into a vein, the muscle twitch response to the stimulation decreases. This dose-dependent decrease is measured. Likewise, the onset and duration of this action can be determined, and compared with those of known, clinically used agents. Electromyographic and mechanomyographic methods are both acceptable.

The invention will be better understood by reference to the following examples which are included merely for purposes of illustration and are not to be construed as limiting the scope of the present invention.

The following example illustrates Synthetic Pathway A.

EXAMPLE 1

Preparation of bis-tropan-3-yl succinate

To a solution of 14.1 g (100 mmol) of tropine in 50 mL of methylene chloride is added dropwise 7.75 g (50 mmol) of succinyl chloride in 100 mL of methylene chloride with cooling in an ice bath. Then the mixture is allowed to warm to room temperature. After the reaction mixture is poured into 200 mL of cold water, the aqueous layer is adjusted to pH 10–11 with 6 N NaOH aqueous solution and extracted with chloroform. The resulting oil is purified by column chromatography (silica gel, 20% methanol in chloroform) to yield 11.8 g (65%) of bis-tropan-3-yl succinate as a thick oil.

Similarly, by substituting:
malonyl chloride
glutaryl chloride
thiodiglycolyl chloride
2-ketoglutaryl chloride
adipoyl chloride
sebacyl chloride
4,4'- dithiodibutyryl chloride
1,11- undecanedicarbonyl dichloride
fumaryl chloride
trans-traumatyl chloride
acetylenedicarbonyl chloride
trans-1,2-cyclobutanedicarbonyl dichloride
1,3-cyclohexanedicarbonyl dichloride
1,1-cyclopentanediacetyl dichloride
phthaloyl chloride
4,5-dichlorophthaloyl chloride
trans-3,6-endomethylene-1,2,3,6-tetrahydrophthaloyl chloride one can obtain:
bis(tropan-3-yl) malonate
bis(tropan-3-yl) glutarate
bis(tropan-3-yl) thiodiglycolate
bis(tropan-3-yl) 2-ketoglutarate
bis(tropan-3-yl) adipate
bis(tropan-3-yl) sebacate
bis(tropan-3-yl) 4,4'-dithiodibutyrate
bis(tropan-3-yl) 1,11-undecanedicarboxylate
bis(tropan-3-yl) fumarate
bis(tropan-3-yl) trans-traumate
bis(tropan-3-yl) acetylenedicarboxylate
bis(tropan-3-yl) cyclobutane-1,2-dicarboxylate
bis(tropan-3-yl) cyclohexane-1,3-dicarboxylate
bis(tropan-3-yl) cyclopentane-1,1'-diacetate
bis(tropan-3-yl) phthalate
bis(tropan-3-yl) 4,5-dichlorophthalate
bis(tropan-3-yl) trans-3,6-endomethylene-1,2,3,6-tetrahydrophthalic Similarly, by substituting other cyclic aminoalkanols for tropine as indicated in formulae 1/a, 1/b and 1/c as starting material and the acyl chlorides listed, one can obtain the corresponding dicarboxylic acid esters.

EXAMPLE 2

Preparation of bis-[N-(3,4-diacetoxybenzyl) tropanium-3-yl] succinate dibromide

To a solution of 5.0 g (13.7 mmol) of bis-tropan-3-yl succinate in 100 mL of dry acetone is added 9.8 g (34.3 mmol) of 3,4-diacetoxybenzyl bromide (prepared from 3,4-dihydroxybenzaldehyde through acetylation of the hydroxy groups, reduction of the aldehyde to the corresponding alcohol, and bromination). Then the mixture is heated at 60–70° C. for 10 hours. The precipitate is collected by filtration, washing with acetone and ether, and drying under vacuum to yield 9.6 g (75%) of bis-[N-(3,4-diacetoxybenzyl)tropanium-3-yl] succinate dibromide as a white powder, which is further purified by recrystallization with methanol-methylene chloride.

Similarly by substituting, for example:
2,5-diacetoxybenzyl bromide
3,4,5-triacetoxybenzyl bromide
3,4-dipropionyloxybenzyl bromide
2,4-dibutyryloxybenzyl bromide
4-acetoxy-3-methoxybenzyl bromide
4-acetoxy-3,5-dimethoxybenzyl bromide
2,5-dimethoxybenzyl bromide
3,4,5-trimethoxybenzyl bromide
3,4-diethoxybenzyl bromide
3,4-diacetoxyphenylethyl bromide
3-(3,4-diacetoxyphenyl)propenyl bromide
and 3,5-diacetoxy-2-naphthylmethyl bromide,
one can prepare:
bis[N-(2,5-diacetoxybenzyl) tropanium-3-yl] succinate dibromide
bis[N-(3,4,5-triacetoxybenzyl) tropanium-3-yl] succinate dibromide
bis[N-(3,4-dipropionyloxybenzyl) tropanium-3-yl] succinate dibromide
bis[N-(2,4-dibutyryloxybenzyl) tropanium-3-yl] succinate dibromide
bis[N-(4-acetoxy-3-methoxybenzyl) tropanium-3-yl] succinate dibromide
bis[N-(4-acetoxy-3,5-dimethoxybenzyl) tropanium-3-yl] succinate dibromide
bis[N-(2,5-dimethoxybenzyl) tropanium-3-yl] succinate dibromide
bis[N-(3,4,5-trimethoxybenzyl) tropanium-3-yl] succinate dibromide
bis[N-(3,4-diethoxybenzyl) tropanium-3-yl] succinate dibromide
bis[N-(3,4-diacetoxyphenylethyl) tropanium-3-yl] succinate dibromide
bis[N-(3-(3,4-diacetoxyphenyl)propenyl) tropanium-3-yl] succinate dibromide, and
bis[N'-(3,5-diacetoxy-2-naphthylmethyl) tropanium-3-yl] succinate dibromide.

It will be realized by one skilled in the art that both starting materials could be substituted. For example if 4-acetoxy-3-methoxybenzyl bromide is substituted for 3,4-diacetoxybenzyl bromide and bis-tropan-3-yl glutarate, bis-tropan-3-yl sebacate, and bis-tropan-3-yl cyclobutane-1,2-dicarboxylate are substituted for bis-tropan-3-yl succinate, then one obtains: bis [N-(4-acetoxy-3-methoxybenzyl) tropanium-3-yl] glutarate dibromide, bis-[N-(4-acetoxy-3-methoxybenzyl)tropanium-3-yl] sebacate dibromide, and bis-[N-(4-acetoxy-3-methoxybenzyl)tropanium-3-yl] cyclobutane-1,2-dicarboxylate dibromide.

The following example illustrates Synthetic Pathway B.

EXAMPLE 3

Preparation of N-(3,4,5-trimethoxybenzyl) tropinium chloride

The mixture of 14.1 g (100 mmol) of tropine and 26.0 g (120 mmol) of 3,4,5-trimethoxybenzyl chloride in 300 mL of acetone is heated at 60–70° C. for 10 hours in a sealed tube. The precipitate is then filtered, washed, and recrystallized to yield 28.6 g (80%) of N-(3,4,5-trimethoxybenzyl) tropinium chloride as a white powder.

Similarly, by substituting, for example:
2-methoxy-5-nitrobenzyl bromide
4-acetoxy-3,5-dimethoxybenzyl chloride
3-(3,4-dipropionyloxyphenyl)propyl bromide
3,5-diacetoxy-2-naphtylmethyl bromide
4-acetoxy-3-chlorobenzyl bromide
one can prepare:
N-(2-methoxy-5-nitrobenzyl) tropinium bromide
N-(4-acetoxy-3,5-dimethoxybenzyl) tropinium chloride
N-(3-(3,4 dipropionyloxyphenyl)propyl) tropinium bromide
N-(3,5 diacetoxy-2-naphthylmethyl) tropinium bromide
N-(4-acetoxy-3-chlorobenzyl) tropinium bromide

EXAMPLE 4

Preparation of bis-[N-(3,4,5-trimethoxybenzyl) tropanium-3-yl] succinate dichloride N-(3,4,5-Trimethoxybenzyl)tropinium chloride (20.0 g, 56.0 mmol) and 4.35 g (28.0 mmol) of succinyl chloride in 100 mL of dry methylene chloride are heated at 100° C. for 12 hours in a sealed tube. After 5 mL of methanol is added to the cooled reaction mixture, solvent is removed on a rotary evaporator. The product is purified by recrystallization from methanol-methylene chloride, yielding 12.0 g (54%) of bis [N-(3,4,5-trimethoxybenzyl)tropanium-3-yl] succinate dichloride.

Similarly by substituting, for example:
N-(2 methoxy-5-nitrobenzyl) tropinium bromide
N-[3-(3,4-dipropionyloxyphenyl)propyl] tropinium bromide
N-(3,5-diacetoxy-2-naphthylmethyl) tropinium bromide
N-(4-acetoxy-3,5-dimethoxybenzyl) tropinium chloride
N-(4-acetoxy-3-chlorobenzyl) tropinium bromide
for N-(3,4,5-trimethoxybenzyl)tropinium chloride,
one can prepare:
bis [N-(2-methoxy-5-nitrobenzyl) tropanium-3-yl] succinate dibromide
bis [N-(3-(3,4-dipropionyloxyphenyl)propyl) tropanium-3-yl] succinate dibromide
bis [N-(3,5-diacetoxy-2-naphthylmethyl) tropanium-3-yl] succinate dibromide
bis [N-(4-acetoxy-3,5-dimethoxybenzyl)tropanium-3-yl] succinate dichloride
bis [N-(4-acetoxy-3-chlorobenzyl)tropanium-3-yl] succinate dibromide The following example illustrates the preparation of an asymmetrical diammonium ester.

EXAMPLE 5

Preparation of [N-(2,5dimethoxybenzyl)tropanium-3-yl], [N-(3,4-diacetoxybenzyl)tropanium-3yl] succinate dibromide To a solution of 18.2 g (50 mmol) of bis(tropan-3-yl) succinate in 500 mL of dry acetone in a sealed bottle is added 11.6 g (50 mmol) of 2,5-dimethoxybenzyl bromide. After the mixture is heated at 50° C. for 24 hours, 14.3 g (50 mmol) of 3,4-diacetoxybenzyl bromide is added to the cooled mixture. Then the mixture is heated again at 70–75° C. for another 10 hours. The resulting white precipitate is collected by filtration, and purified by recrystallization (2×) from MeOH-methylene chloride to yield 9.0 g (20%) of [N-(2,5-dimethoxybenzyl)tropanium-3-yl], [N-(3,4-diacetoxybenzyl)tropanium-3-yl] succinate dibromide as a white powder.

Similarly, for example, by substituting 3,4-dibromophenethyl bromide and 3-(4,6-dimethoxynaphth-2-yl)propenyl bromide for 2,5-dimethoxybenzyl bromide and 3,4-diacetoxybenzyl bromide, respectively, one can obtain [N-(3,4-dibromophenethyl)tropanium-3-yl], [N-{3-(4,6-dimethoxynaphth-2-yl)propenyl}tropanium-3-yl] succinate dibromide.

The following example illustrates Synthetic Pathway C.

EXAMPLE 6

Preparation of bis[quinuclidin-3-yl] trans-3,6-endomethylene-1,2,3,6-tetrahydrophthalate To a solution of trans-3,6-endomethylene-1,2,3,6-tetrahydrophthaloyl chloride (2.63 g. 12.0 mmol) in 20 mL of methylene chloride in a sealed tube is added 3-quinuclidinol hydrochloride (4.50 g, 27.5 mmol). The heterogeneous mixture is heated to 80° C. overnight. After it is cooled, the mixture is poured into 100 mL of 2 N NaOH aqueous solution, and extracted with $CHCl_3$. The combined organic layer is dried over $MgSO_4$ and concentrated. The resulting oil is purified by column chromatography (silica gel, 10% MeOH in $CHCl_3$) to yield 4.0 g (83%) of bis [quinuclidin-3-yl] trans-3,6-endomethylene-1,2,3,6-tetrahydrophthalate as a white solid.

EXAMPLE 7

Preparation of bis[N-(4-acetoxy-3-methoxybenzyl) quinuclidinium-3-yl] trans-3,6-endomethylene-1,2,3, 6-tetrahydrophthalate dibromide A solution of bis[quinuclidin-3-yl] trans-3,6-endomethylene-1,2,3,6-tetrahydrophthalate (1.0 g, 2.5 mmol) and 4-acetoxy-3-methoxybenzyl bromide (1.6 g, 6.25 mmol) in 30 mL of acetone is heated at 60° C. in a sealed tube for 10 hours. The white solid (1.22 g, 54%) precipitated out is collected by a vacuum for 1 hour.

Elemental analysis of this compound and other representative compounds are shown in Table 1, wherein C, H, and N are shown as weight %. High resolution mass data and melting points are shown in Table 2.

Similarly, by appropriate choices of starting materials other symmetric and asymmetric bis quaternary ammonium salts of the general structures of 1/a, 1/b and 1/c can be made, for example:

[N-ethyl, N-(4-acetoxy-3,5-dimethoxybenzyl) nor-granataninium-3-yl], [N-ethyl, N-(3,5-dinitrobenzyl) nor-granataninium-3-yl] cyclobutane-1,2-dicarboxylate dibromide, bis [N-(2,5-dimethoxybenzyl) quinuclidinium-3-yl] isophthalate dibromide, bis[N-(3,4-dipropionyloxyphenethyl) 1,2,6-trimethylpiperidinium-4-yl] cyclopentane-1,1-dibutyrate dibromide.

TABLE 1

ELEMENTAL ANALYSIS

| New Compounds: | Formula | Calculated Value C | Calculated Value H | Calculated Value N | Observed Value C | Observed Value H | Observed Value N |
|---|---|---|---|---|---|---|---|
| bis[N-(4-acetoxy-3-methoxybenzyl) quinuclidinium-3-yl] trans-3,6-endomethylene-1,2,3,6-tetrahydrophthalate dibromide | C43H54N2O10Br2.3H2O | 53.09 | 6.17 | 2.88 | 53.51 | 6.55 | 2.93 |
| bis[N-(2,5-dimethoxybenzyl) tropanium-3α-yl] trans-3,6-endomethylene-1,2,3,6-tetrahydrophthalate dibromide | | | | | | | |
| bis[N-(3,4,5-trimethoxybenzyl) tropanium-3αyl] 1,9-nonanedicarboxylate dibromide | | | | | | | |
| bis[N-(4-acetoxy-3,5-dimethoxybenzyl) tropanium-3α-yl] trans-3,6-endomethylene-1,2,3,6-tetrahydrophthalate dibromide | C47H62N2O12Br2.H2O | 55.08 | 6.25 | 2.73 | 54.36 | 6.45 | 2.73 |
| bis[N-(4-acetoxy-3,5-dimethoxybenzyl) tropanium-3α-yl] cyclobutane-1,2-dicarboxylate dibromide | C48H68N2O12Br2.H2O | 55.28 | 6.72 | 2.68 | 54.14 | 6.57 | 2.77 |
| bis[N-(3,5-dimethoxy-4-propionyloxybenzyl) tropanium-3α-yl] cyclohexane-1,3-dicarboxylate dibromide | C45H58N2O10Br2.H2O | 56.02 | 6.22 | 2.90 | 54.71 | 6.12 | 2.88 |
| bis[N-(4-acetoxy-3-methoxybenzyl) tropanium-3α-yl] trans-3,6-endomethylene-1,2,3,6-tetrahydrophthalate dibromide | C42H56N2O10Br2.H2O | 54.42 | 6.26 | 3.02 | 52.75 | 6.57 | 3.04 |
| bis[N-(4-acetoxy-3-methoxybenzyl) tropanium-3α-yl] cyclobutane-1,2-dicarboxylate dibromide | C44H60N2O10Br2.H2O | 55.34 | 6.50 | 2.94 | 53.93 | 6.59 | 3.07 |
| bis[N-(4-acetoxy-3-methoxybenzyl) tropanium-3α-yl] cyclohexane-1,3-dicarboxylate dibromide | C47H58N2O12Br2.2H2O | 53.41 | 6.06 | 2.65 | 53.51 | 6.55 | 2.93 |
| bis[N-(3,4-diacetoxybenzyl) tropanium-3α-yl] trans-3,6-endomethylene-1,2,3,6-tetrahydrophthalate dibromide | C44H56N2O12Br2.2H2O | 52.80 | 6.00 | 2.80 | 52.50 | 6.26 | 2.89 |
| bis[N-(3,4-diacetoxybenzyl) tropanium-3α-yl] cyclobutane-1,2-dicarboxylate dibromide | C46H60N2O12Br2.H2O | 54.76 | 6.15 | 2.78 | 53.05 | 6.35 | 2.85 |
| bis[N-(3,4-diacetoxybenzyl) tropanium-3α-yl] cyclohexane-1,3-dicarboxylate dibromide | C43H56N2O12Br2.H2O | 53.20 | 5.98 | 2.89 | 52.08 | 6.32 | 3.00 |
| bis[N-(3,4-diacetoxybenzyl) tropanium-3β-yl] trans-3,6-endomethylene-1,2,3,6-tetrahydrophthalate dibromide | C47H58N2O12Br2.H2O | 55.29 | 5.88 | 2.75 | 54.87 | 5.99 | 2.89 |
| bis[N-(3,4-diacetoxybenzyl) granataninium-3-yl] trans-3,6-endomethylene-1,2,3,6-tetrahydrophthalate dibromide | C45H60N2O12Br2.H2O | 54.10 | 6.21 | 2.81 | 53.62 | 6.20 | 2.91 |
| bis[N-(3,4-diacetoxybenzyl) granataninium-3-yl] glutarate dibromide | C46H62N2O12Br2 | 55.53 | 6.24 | 2.82 | 53.71 | 6.25 | 3.04 |
| bis[N-(3,4-diacetoxybenzyl) granataninium-3-yl] adipate dibromide | C47H64N2O12Br2 | 55.95 | 6.36 | 2.78 | 53.60 | 6.29 | 2.69 |
| bis[N-(3,4-diacetoxybenzyl) granataninium-3-yl] pimelate dibromide | C48H66N2O12Br2 | 56.36 | 6.46 | 2.74 | 54.89 | 6.40 | 2.88 |
| bis[N-(3,4-diacetoxybenzyl) granataninium-3-yl] suberate dibromide | C48H66N2O12Br2 | 56.36 | 6.46 | 2.74 | 54.89 | 6.40 | 2.88 |
| bis[N-(3,4-diacetoxybenzyl) granataninium-3-yl] cyclobutane-1,2-dicarboxylate dibromide | C46H60N2O12Br2.H2O | 54.65 | 6.14 | 2.77 | 52.53 | 6.13 | 2.85 |
| bis[N-(3,4-dipropionyloxybenzyl) tropanium-3α-yl] glutarate dibromide | C47H64N2O12Br2.H2O | 54.97 | 6.43 | 2.73 | 54.66 | 6.42 | 2.94 |
| bis[N-(3,4-dipropionyloxybenzyl) tropanium-3α-yl] adipate dibromide | C48H66N2O12Br2 | 56.36 | 6.46 | 2.74 | 56.00 | 6.40 | 2.88 |
| bis[N-(3,4-dipropionyloxybenzyl) tropanium-3α-yl] cyclobutane-1,2-dicarboxylate dibromide | C48H64N2O12Br2 | 56.47 | 6.27 | 2.75 | 54.30 | 6.25 | 2.81 |
| bis[N-(3,4-dipropionyloxybenzyl) granataninium-3-yl] glutarate dibromide | C49H68N2O12Br2.H2O | 55.78 | 6.64 | 2.66 | 55.00 | 6.38 | 2.78 |
| bis[N-(3,4-dipropionyloxybenzyl) granataninium-3-yl] adipate dibromide | C50H70N2O12Br2.H2O | 56.18 | 6.74 | 2.62 | 56.09 | 6.79 | 2.76 |
| bis[N-(3,4-dipropionyloxybenzyl) granataninium-3-yl] pimelate dibromide | C51H72N2O12Br2 | 57.52 | 6.77 | 2.63 | 57.16 | 6.69 | 2.77 |
| bis[N-(3,4-dipropionyloxybenzyl) granataninium-3-yl] cyclobutane-1,2-dicarboxylate dibromide | C50H68N2O12Br2.H2O | 56.29 | 6.56 | 2.62 | 55.92 | 6.34 | 2.82 |

TABLE 2

High Resolution Mass Data and Melting Point

| New Compounds: | High Resolution Mass Formula | calculated | found | Melting Point (°C.) |
|---|---|---|---|---|
| bis[N-(4-acetoxy-3-methoxybenzyl) quinuclidinium-3-yl] trans-3,6-endomethylene-1,2,3,6-tetrahydrophthalate dibromide | C43H54N2O10Br | 837.2962 | 837.2961 | 229–231 |
| bis[N-(2,5-dimethoxybenzyl) tropanium-3α-yl] trans-3,6-endomethylene-1,2,3,6-tetrahydrophthalate dibromide | | | | 192–194 |
| bis[N-(3,4,5-trimethoxybenzyl) tropanium-3α-yl] 1,9-nonanedicarboxylate dibromide | | | | 184–185 |
| bis[N-(4-acetoxy-3,5-dimethoxybenzyl) tropanium-3α-yl] 1,9-nonanedicarboxylate dibromide | | | | 230–231 |
| bis[N-(4-acetoxy-3,5-dimethoxybenzyl) tropanium-3α-yl] trans-3,6-endomethylene-1,2,3,6-tetrahydrophthalate dibromide | | | | 223–224 |
| bis[N-(4-acetoxy-3,5-dimethoxybenzyl) tropanium-3α-yl] cyclobutane-1,2-dicarboxylate dibromide | | | | 233–231 |
| bis[N-(3,5-dimethoxy-4-propionyloxybenzyl) tropanium-3α-yl] cyclohexane-1,3-dicarboxylate dibromide | | | | 233–234 |
| bis[N-(4-acetoxy-3-methoxybenzyl) tropanium-3α-yl] trans-3,6-endomethylene-1,2,3,6-tetrahydrophthalate dibromide | C45H58N2O10Br | 865.3275 | 865.3275 | 212–213 |
| bis[N-(4-acetoxy-3-methoxybenzyl) tropanium-3α-yl] cyclobutane-1,2-dicarboxylate dibromide | C42H56N2O10Br | 827.3118 | 827.3102 | 203–204 |
| bis[N-(4-acetoxy-3-methoxybenzyl) tropanium-3α-yl] cyclohexane-1,3-dicarboxylate dibromide | C44H60N2O10Br | 857.3411 | 857.3449 | 215–216 |
| bis[N-(3,4-diacetoxybenzyl) tropanium-3α-yl] trans-3,6-endomethylene-1,2,3,6-tetrahydrophthalate dibromide | C47H58N2O12Br | 921.3173 | 921.3178 | 219–220 |
| bis[N-(3,4-diacetoxybenzyl) tropanium-3α-yl] cyclobutane-1,2-dicarboxylate dibromide | C44H56N2O12Br | 833.3017 | 833.3027 | 205–206 |
| bis[N-(3,4-diacetoxybenzyl) tropanium-3α-yl] cyclohexane-1,3-dicarboxylate dibromide | C46H60N2O12Br | 911.3331 | 911.3335 | 211–212 |
| bis[N-(3,4-diacetoxybenzyl) tropanium-3α-yl] glutarate dibromide | C43H56N2O12Br | 873.2996 | 873.2996 | 200–201 |
| bis[N-(3,4-diacetoxybenzyl) tropanium-3β-yl] trans-3,6-endomethylene-1,2,3,6-tetrahydrophthalate dibromide | C45H60N2O12Br | 899.3331 | 899.3353 | 218–219 |
| bis[N-(3,4-diacetoxybenzyl) granataninium-3-yl] glutarate dibromide | C46H62N2O12Br | 913.3486 | 913.3491 | 186–187 |
| bis[N-(3,4-diacetoxybenzyl) granataninium-3-yl] adipate dibromide | C47H64N2O12Br | 927.3643 | 927.3655 | 180–181 |
| bis[N-(3,4-diacetoxybenzyl) granataninium-3-yl] pimelate dibromide | C48H66N2O12Br | 941.3799 | 941.3784 | 185–186 |
| bis[N-(3,4-diacetoxybenzyl) granataninium-3-yl] suberate dibromide | C46H60N2O12Br | 911.3331 | 911.3337 | 195–196 |
| bis[N-(3,4-diacetoxybenzyl) granataninium-3-yl] cyclobutane-1,2-dicarboxylate dibromide | C47H64N2O12Br | 927.3643 | 927.3651 | 194–195 |
| bis[N-(3,4-dipropionyloxybenzyl) tropanium-3α-yl] glutarate dibromide | C48H66N2O12Br | 941.3801 | 941.3785 | 212–213 |
| bis[N-(3,4-dipropionyloxybenzyl) tropanium-3α-yl] adipate dibromide | C48H64N2O12Br | 939.3643 | 939.3659 | 221–222 |
| bis[N-(3,4-dipropionyloxybenzyl) granataninium-3-yl] cyclobutane-1,2-dicarboxylate dibromide | C49H68N2O12Br | 955.3956 | 955.3951 | 218–219 |
| bis[N-(3,4-dipropionyloxybenzyl) granataninium-3-yl] glutarate dibromide | C50H70N2O12Br | 969.4112 | 969.4086 | 200–201 |
| bis[N-(3,4-dipropionyloxybenzyl) granataninium-3-yl] adipate dibromide | C51H72N2O12Br | 983.4269 | 983.4285 | 208–209 |
| bis[N-(3,4-dipropionyloxybenzyl) granataninium-3-yl] pimelate dibromide | C50H68N2O12Br | 967.3956 | 967.3957 | 203–204 |
| bis[N-(3,4-dipropionyloxybenzyl) granataninium-3-yl] cyclobutane-1,2-dicarboxylate dibromide | | | | 199–200 |

EXAMPLE 8

In Vivo Animal Testing of the Biological Activity of Neuromuscular Blocking Agents The neuromuscular blocking activity and other effects (e.g. cardiovascular side effects) of selected agents were investigated on several different experimental animals. Justification for this approach lies in the commonly known fact that the pharmacodynamic and pharmacokinetic properties of these agents are markedly variable from species to species. Therefore, the most important aspects of the projected therapeutic utility of these agents, e.g., neuromuscular blocking potency, onset and duration of action, and side effects cannot be ascertained in "in vitro" preparations or by using only one species of animals.

Selected compounds of the present invention have been carefully investigated, first in "screening" experiments in rats, for determining neuromuscular blocking potency. Subsequently, selected compounds have been tested for specific effects, e.g. onset, duration of action, and side effects, on additional selected species of animals, such as cats, pigs, monkeys, rabbits and dogs.

The following is a description of the methods as used in the rat and the cat. These methods were also utilized on other species when needed.

a) Adult, male albino rats were anesthetized with pentobarbital injected intraperitoneally. The trachea was cannulated for artificial respiration via a small animal respirator. The carotid artery was cannulated for recording blood pressure via a transducer and heart rate by a cardiotachograph on a polygraph. One external jugular vein was cannulated for i.v. drug administration. Neuromuscular function was monitored by electromyography, recording evoked responses from the anterior tibial muscle as a result of supramaximal nerve stimuli consisting of single or "train-of-four" rectangular pulses of 0.1–0.2 msec duration every 10–12 seconds, delivered to the sciatic or common peroneal nerve by a laboratory nerve stimulator. Another mode of stimulation included repeated single stimuli delivered at 0.1 Hz or 1 Hz. Cardiac vagal block, a side effect of several muscle relaxant agents, was assessed by stimulating the cut cervical vagus nerve peripherally and determining the possible blocking effect against the vagally induced bradycardia. The agents were dissolved in physiologic saline and injected intravenously at appropriate time intervals. The intensity, onset, and duration of neuromuscular block and its type were determined with each agent. Through administering several doses, the doses corresponding to 50%, 80% and 90% neuromuscular block were determined. All agents were compared with selected standard neuromuscular blocking compounds, e.g. succinylcholine, pancuronium, mivacurium, or rocuronium. The resulting data are shown in Table 3, wherein:

ED50=intravenous dose, ug/kg, causing 50% neuromuscular block.

Onset=time in minutes to 80–85% neuromuscular block.

RI=recovery index, minutes, spontaneous recovery, 25–75% neuromuscular response.

VB=vagal block, %, at 80–85% neuromuscular blocking dose.

$\Delta$HR=change in heart rate, %, at 80–85% neuromuscular blocking dose.

$\Delta$BP=change in arterial blood pressure, %, at 80–85% neuromuscular blocking dose.

No=number of animals tested.

b) Adult cats were anesthetized with a mixture of 70 mg/kg alpha chloralose and 0.5 g/kg ethylurethane intraperitoneally. One thigh was fixed in a vertical position by means of a pin at the lower end of the femur. Needle electrodes were placed on the sciatic or the common peroneal nerve. A tendon of the anterior tibial muscle was attached to a force transducer and the muscle responses evoked, as described under a), were recorded. Both electromyographic and mechanomyographic responses can be quantified. Blood pressure and heart rate changes were recorded from appropriately cannulated arteries via a blood pressure transducer and cardiotachograph. The resulting data are shown in Table 4.

The techniques described under a) and b) were employed in other species as needed with the modification that juvenile pigs were initially anesthetized with inhalation of halothane (Table 5) and monkeys were initially sedated with intramuscular ketamine injections prior to inducing and maintaining general anesthesia using pentobarbital and propofol administered intravenously (Table 6). Rabbit data are shown in Table 7 and dog data are shown in Table 8.

All animal experiments considered together, these novel neuromuscular relaxants are 2–10 times faster and shorter acting than the comparison compounds.

BRIEF DESCRIPTION OF THE DRAWING

FIG. 1 illustrates the neuromuscular blocking effect of bis[N-(3,4-diacetoxybenzyl) tropanium-3-yl] cyclobutane-1,2-dicarboxylate dibromide as compared with succinylcholine and rocuronium in the monkey. Shown are the EMG response for muscle relaxation and the blood pressure response against time in minutes.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

TABLE 3

| RAT | ED50 | Onset | RI | VB | ΔH | ΔBP | No |
|---|---|---|---|---|---|---|---|
| New Compounds: | | | | | | | |
| bis[N-(4-acetoxy-3-methoxybenzyl) quinuclidinium-3-yl] trans-3,6-endomethylene-1,2,3,6-tetrahydrophthalate dibromide | 2000 | 1.8 | 3 | 70 | −5 | −10 | 3 |
| bis[N-(2,5-dimethoxybenzyl) tropanium-3α-yl] trans-3,6-endomethylene-1,2,3,6-tetrahydrophthalate dibromide | 57 | 1 | 1.9 | 32 | 0 | 0 | 5 |
| bis[N-(3,4,5-trimethoxybenzyl) tropanium-3α-yl] 1,9-nonanedicarboxylate dibromide | 180 | 0.8 | 1.8 | 10 | 0 | 0 | 5 |
| bis[N-(4-acetoxy-3,5-dimethoxybenzyl) tropanium-3α-yl] 1,9-nonanedicarboxylate dibromide | 500 | 0.4 | 0.5 | 99 | 0 | 0 | 3 |
| bis[N-(4-acetoxy-3,5-dimethoxybenzyl) tropanium-3α-yl] trans-3,6-endomethylene-1,2,3,6-tetrahydrophthalate dibromide | 200 | 0.7 | 0.8 | 20 | 0 | 0 | 7 |
| bis[N-(4-acetoxy-3,5-dimethoxybenzyl) tropanium-3α-yl] cyclobutane-1,2-dicarboxylate dibromide | 367 | 0.4 | 0.45 | 20 | 0 | 0 | 3 |
| bis[N-(3,5-dimethoxy-4-propionyloxybenzyl) tropanium-3α-yl] trans-3,6-endomethylene-1,2,3,6-tetrahydrophthalate dibromide | 270 | 0.55 | 0.45 | 0 | 0 | 0 | 3 |
| bis[N-(4-acetoxy-3-methoxybenzyl) tropanium-3α-yl] cyclohexane-1,2-dicarboxylate dibromide | 150 | 0.55 | 0.5 | 25 | 0 | 0 | 7 |
| bis[N-(4-acetoxy-3-methoxybenzyl) tropanium-3α-yl] cyclohexane-1,3-dicarboxylate dibromide | 350 | 0.6 | 0.5 | 20 | 0 | 0 | 4 |
| bis[N-(4-acetoxy-3-methoxybenzyl) tropanium-3α-yl] trans-3,6-endomethylene-1,2,3,6-tetrahydrophthalate dibromide | 270 | 0.55 | 0.45 | 30 | 0 | 0 | 7 |
| bis[N-(3,4-diacetoxybenzyl) tropanium-3α-yl] trans-3,6-endomethylene-1,2,3,6-tetrahydrophthalate dibromide | 84 | 0.65 | 0.5 | 32 | 0 | 0 | 11 |
| bis[N-(3,4-diacetoxybenzyl) tropanium-3α-yl] cyclobutane-1,2-dicarboxylate dibromide | 218 | 0.7 | 0.45 | 5 | 0 | 0 | 10 |
| bis[N-(3,4-diacetoxybenzyl) tropanium-3α-yl] cyclohexane-1,3-dicarboxylate dibromide | 240 | 0.65 | 0.5 | 28 | 0 | 0 | 9 |
| bis[N-(3,4-diacetoxybenzyl) tropanium-3α-yl] glutarate dibromide | 232 | 0.75 | 0.6 | 10 | 0 | 0 | 9 |
| bis[N-(3,4-diacetoxybenzyl) tropanium-3β-yl] trans-3,6-endomethylene-1,2,3,6-tetrahydrophthalate dibromide | 258 | 0.68 | 0.5 | 45 | 0 | 0 | 4 |
| bis[N-(3,4-diacetoxybenzyl) granataninium-3-yl] glutarate dibromide | 170 | 0.6 | 0.45 | 0 | 0 | 0 | 7 |
| bis[N-(3,4-diacetoxybenzyl) granataninium-3-yl] adipate dibromide | 140 | 0.5 | 0.4 | 5 | 0 | 0 | 14 |
| bis[N-(3,4-diacetoxybenzyl) granataninium-3-yl] pimelate dibromide | 175 | 0.45 | 0.4 | 0 | 0 | 0 | 8 |
| bis[N-(3,4-diacetoxybenzyl) granataninium-3-yl] suberate dibromide | 450 | 0.4 | 0.35 | 60 | 0 | 0 | 3 |
| bis[N-(3,4-diacetoxybenzyl) granataninium-3-yl] cyclobutane-1,2-dicarboxylate dibromide | 133 | 0.5 | 0.4 | 2 | 0 | 0 | 3 |
| bis[N-(3,4-dipropionyloxybenzyl) tropanium-3α-yl] glutarate dibromide | 300 | 0.7 | 0.5 | 0 | 0 | 0 | 4 |
| bis[N-(3,4-dipropionyloxybenzyl) tropanium-3α-yl] adipate dibromide | 217 | 0.6 | 0.4 | 18 | 0 | 0 | 8 |
| bis[N-(3,4-dipropionyloxybenzyl) tropanium-3α-yl] cyclobutane-1,2-dicarboxylate dibromide | 238 | 0.6 | 0.6 | 17 | 0 | 0 | 5 |
| bis[N-(3,4-dipropionyloxybenzyl) granataninium-3-yl] glutarate dibromide | 260 | 0.55 | 0.4 | 0 | 0 | 0 | 5 |
| bis[N-(3,4-dipropionyloxybenzyl) granataninium-3-yl] adipate dibromide | 320 | 0.4 | 0.35 | 0 | 0 | −4 | 2 |
| bis[N-(3,4-dipropionyloxybenzyl) granataninium-3-yl] pimelate dibromide | 450 | 0.5 | 0.35 | 2 | −3 | −6 | 3 |
| bis[N-(3,4-dipropionyloxybenzyl) granataninium-3-yl] cyclobutane-1,2-dicarboxylate dibromide | 155 | 0.45 | 0.35 | 0 | 0 | 0 | 8 |
| Comparison Compounds: | | | | | | | |
| Rocuronium | 450 | 0.95 | 1.3 | 60 | 0 | 0 | 7 |
| Mivacurium | 140 | 1.8 | 3.9 | 0 | 0 | 0 | 8 |
| Atracurium | 320 | 1.5 | 2.9 | 0 | 0 | 0 | 5 |
| bis[N-methyl tropanium-3α-yl] glutarate diiodide | 2000 | 1.2 | 4.2 | 100 | 0 | 0 | 4 |
| bis[N-methyl tropanium-3α-yl] glutarate dibromide | 5500 | 2.5 | 3.7 | 100 | 0 | −10 | 4 |
| bis[N-(2-bromobenzyl) tropanium-3α-yl] glutarate dibromide | 1400 | 2.3 | 3.6 | 100 | 0 | −9 | 5 |

TABLE 4

| Cat | ED50 | Onset | RI | VB | ΔH | ΔBP | No |
|---|---|---|---|---|---|---|---|
| New Compounds: | | | | | | | |
| bis[N-(4-acetoxy-3-methoxybenzyl) quinuclidinium-3-yl] trans-3,6-endomethylene-1,2,3,6-tetrahydrophthalate dibromide | | | | | | | |
| bis[N-(2,5-dimethoxybenzyl) tropanium-3α-yl] trans-3,6-endomethylene-1,2,3,6-tetrahydrophthalate dibromide | | | | | | | |
| bis[N-(3,4,5-trimethoxybenzyl) tropanium-3α-yl] 1,9-nonanedicarboxylate dibromide | | | | | | | |
| bis[N-(4-acetoxy-3,5-dimethoxybenzyl) tropanium-3α-yl] 1,9-nonanedicarboxylate dibromide | | | | | | | |
| bis[N-(4-acetoxy-3,5-dimethoxybenzyl) tropanium-3α-yl] trans-3,6-endomethylene-1,2,3,6-tetrahydrophthalate dibromide | | | | | | | |
| bis[N-(4-acetoxy-3,5-dimethoxybenzyl) tropanium-3α-yl] cyclobutane-1,2-dicarboxylate dibromide | | | | | | | |
| bis[N-(3,5-dimethoxy-4-propionyloxybenzyl) tropanium-3α-yl] cyclohexane-1,3-dicarboxylate dibromide | | | | | | | |
| bis[N-(4-acetoxy-3-methoxybenzyl) tropanium-3α-yl] trans-3,6-endomethylene-1,2,3,6-tetrahydrophthalate dibromide | 193 | 0.7 | 0.4 | 20 | 5 | 0 | 3 |
| bis[N-(4-acetoxy-3-methoxybenzyl) tropanium-3α-yl] cyclobutane-1,2-dicarboxylate dibromide | 160 | 0.9 | 0.5 | 20 | 0 | 0 | 3 |
| bis[N-(4-acetoxy-3-methoxybenzyl) tropanium-3α-yl] cyclohexane-1,3-dicarboxylate dibromide | 325 | 0.9 | 0.5 | 33 | 0 | -5 | 2 |
| bis[N-(3,4-diacetoxybenzyl) tropanium-3α-yl] trans-3,6-endomethylene-1,2,3,6-tetrahydrophthalate dibromide | 120 | 0.9 | 0.5 | 30 | -12 | -30 | 2 |
| bis[N-(3,4-diacetoxybenzyl) tropanium-3α-yl] cyclobutane-1,2-dicarboxylate dibromide | 135 | 0.95 | 0.5 | 12 | 0 | 0 | 4 |
| bis[N-(3,4-diacetoxybenzyl) tropanium-3α-yl] cyclohexane-1,3-dicarboxylate dibromide | 110 | 0.8 | 0.5 | 34 | -12 | -25 | 2 |
| bis[N-(3,4-diacetoxybenzyl) tropanium-3α-yl] glutarate dibromide | 183 | 1 | 0.6 | 8 | 0 | 0 | 3 |
| bis[N-(3,4-diacetoxybenzyl) tropanium-3β-yl] trans-3,6-endomethylene-1,2,3,6-tetrahydrophthalate dibromide | | | | | | | |
| bis[N-(3,4-diacetoxybenzyl) granataninium-3-yl] glutarate dibromide | 700 | 0.7 | 0.4 | 60 | 0 | -50 | 1 |
| bis[N-(3,4-diacetoxybenzyl) granataninium-3-yl] adipate dibromide | 400 | 0.7 | 0.5 | 70 | 0 | -40 | 1 |
| bis[N-(3,4-diacetoxybenzyl) granataninium-3-yl] pimelate dibromide | | | | | | | |
| bis[N-(3,4-diacetoxybenzyl) granataninium-3-yl] suberate dibromide | 700 | 0.6 | 0.5 | 80 | 0 | -20 | 1 |
| bis[N-(3,4-diacetoxybenzyl) granataninium-3-yl] cyclobutane-1,2-dicarboxylate dibromide | 400 | 0.6 | 0.5 | | 0 | 0 | 1 |
| bis[N-(3,4-dipropionyloxybenzyl) tropanium-3α-yl] glutarate dibromide | | | | | | | |
| bis[N-(3,4-dipropionyloxybenzyl) tropanium-3α-yl] adipate dibromide | | | | | | | |
| bis[N-(3,4-dipropionyloxybenzyl) tropanium-3α-yl] cyclobutane-1,2-dicarboxylate dibromide | | | | | | | |
| bis[N-(3,4-dipropionyloxybenzyl) granataninium-3-yl] glutarate dibromide | | | | | | | |
| bis[N-(3,4-dipropionyloxybenzyl) granataninium-3-yl] adipate dibromide | | | | | | | |
| bis[N-(3,4-dipropionyloxybenzyl) granataninium-3-yl] pimelate dibromide | | | | | | | |
| bis[N-(3,4-dipropionyloxybenzyl) granataninium-3-yl] cyclobutane-1,2-dicarboxylate dibromide | | | | | | | |
| Comparison Compounds: | | | | | | | |
| Rocuronium | 185 | 2.1 | 3.8 | | 0 | 0 | 6 |
| Mivacurium | 25 | 3.5 | 5 | | 0 | 0 | 6 |
| Atracurium | 68 | 2.7 | 4.8 | | 0 | 0 | 6 |
| bis[N-(cyclopropylmethyl) tropanium-3α-yl] suberate dibromide | 155 | 1.4 | 9 | 80 | 0 | 0 | 5 |
| bis[N-methyl tropanium-3α-yl] sebacate diiodide | 125 | 2.3 | 3.9 | 100 | 0 | 0 | 4 |

TABLE 5

| Pig | ED50 | Onset | RI | VB | ΔH | ΔBP | No |
|---|---|---|---|---|---|---|---|
| New Compounds: | | | | | | | |
| bis[N-(4-acetoxy-3-methoxybenzyl) quinuclidinium-3-yl] trans-3,6-endomethylene-1,2,3,6-tetrahydrophthalate dibromide | 310 | 1.5 | 2.4 | 40 | 0 | 0 | 4 |
| bis[N-(2,5-dimethoxybenzyl) tropanium-3α-yl] trans-3,6-endomethylene-1,2,3,6-tetrahydrophthalate dibromide | 600 | 0.5 | 1.2 | 90 | 0 | 0 | 1 |
| bis[N-(3,4,5-trimethoxybenzyl) tropanium-3α-yl] 1,9-nonanedicarboxylate dibromide | 343 | 0.54 | 2 | 26 | 0 | 0 | 4 |
| bis[N-(4-acetoxy-3,5-dimethoxybenzyl) tropanium-3α-yl] trans-3,6-endomethylene-1,2,3,6-tetrahydrophthalate dibromide | 250 | 0.7 | 1.3 | 30 | 0 | 0 | 1 |
| bis[N-(4-acetoxy-3,5-dimethoxybenzyl) tropanium-3α-yl] cyclobutane-1,2-dicarboxylate dibromide | 190 | 0.6 | 1 | 43 | 0 | 0 | 4 |
| bis[N-(3,5-dimethoxy-4-propionyloxybenzyl) tropanium-3α-yl] cyclohexane-1,3-dicarboxylate dibromide | 268 | 0.5 | 0.87 | 46 | 0 | 0 | 4 |
| bis[N-(4-acetoxy-3-methoxybenzyl) tropanium-3α-yl] trans-3,6-endomethylene-1,2,3,6-tetrahydrophthalate dibromide | 183 | 0.6 | 0.75 | 65 | 0 | 0 | 4 |
| bis[N-(4-acetoxy-3-methoxybenzyl) tropanium-3α-yl] cyclobutane-1,2-dicarboxylate dibromide | 197 | 0.65 | 0.9 | 42 | 0 | 0 | 3 |
| bis[N-(4-acetoxy-3-methoxybenzyl) tropanium-3α-yl] cyclohexane-1,3-dicarboxylate dibromide | 275 | 0.68 | 0.85 | 42 | 0 | 0 | 6 |
| bis[N-(3,4-diacetoxybenzyl) tropanium-3α-yl] trans-3,6-endomethylene-1,2,3,6-tetrahydrophthalate dibromide | 225 | 0.8 | 0.85 | 54 | 0 | 0 | 7 |
| bis[N-(3,4-diacetoxybenzyl) tropanium-3α-yl] cyclobutane-1,2-dicarboxylate dibromide | 230 | 0.95 | 1.1 | 41 | 0 | 0 | 6 |
| bis[N-(3,4-diacetoxybenzyl) tropanium-3α-yl] cyclohexane-1,3-dicarboxylate dibromide | 160 | 1.1 | 2 | 100 | 0 | 0 | 6 |
| bis[N-(3,4-diacetoxybenzyl) tropanium-3β-yl] trans-3,6-endomethylene-1,2,3,6-tetrahydrophthalate dibromide | 235 | 0.8 | 0.9 | 40 | -10 | -5 | 1 |
| bis[N-(3,4-diacetoxybenzyl) granataninium-3-yl] glutarate dibromide | 140 | 0.7 | 0.9 | 51 | 0 | 0 | 4 |
| bis[N-(3,4-diacetoxybenzyl) granataninium-3-yl] adipate dibromide | 193 | 0.7 | 1 | 48 | 0 | 0 | 3 |
| bis[N-(3,4-diacetoxybenzyl) granataninium-3-yl] pimelate dibromide | 250 | 0.6 | 0.8 | 80 | 0 | 0 | 3 |
| bis[N-(3,4-diacetoxybenzyl) granataninium-3-yl] suberate dibromide | 100 | 0.8 | 1 | 15 | 0 | 0 | 3 |
| bis[N-(3,4-diacetoxybenzyl) granataninium-3-yl] cyclobutane-1,2-dicarboxylate dibromide | 450 | 1.1 | 0.6 | 70 | 0 | 0 | 1 |
| bis[N-(3,4-dipropionyloxybenzyl) tropanium-3α-yl] glutarate dibromide | 300 | 0.65 | 0.75 | 65 | 0 | 0 | 2 |
| bis[N-(3,4-dipropionyloxybenzyl) tropanium-3α-yl] adipate dibromide | 317 | 0.7 | 0.6 | 50 | 0 | 0 | 3 |
| bis[N-(3,4-dipropionyloxybenzyl) tropanium-3α-yl] cyclobutane-1,2-dicarboxylate dibromide | 230 | 0.5 | 0.65 | 35 | 0 | 0 | 2 |
| bis[N-(3,4-dipropionyloxybenzyl) granataninium-3-yl] glutarate dibromide | 275 | 0.45 | 0.4 | 43 | 0 | 0 | 2 |
| bis[N-(3,4-dipropionyloxybenzyl) granataninium-3-yl] adipate dibromide | 700 | 0.5 | 0.5 | 30 | 0 | 0 | 1 |
| bis[N-(3,4-dipropionyloxybenzyl) granataninium-3-yl] pimelate dibromide | 190 | 0.5 | 0.4 | 18 | 0 | 0 | 4 |
| bis[N-(3,4-dipropionyloxybenzyl) granataninium-3-yl] cyclobutane-1,2-dicarboxylate dibromide | | | | | | | |
| Comparison Compounds: | | | | | | | |
| Rocuronium | 350 | 1.5 | 3.2 | 47 | 0 | 0 | 7 |
| Mivacurium | 135 | 1.5 | 3.6 | 17 | 0 | 0 | 10 |
| bis[N-(pentyl) tropanium-3α-yl] sebacate dibromide | 300 | 2.00 | 6.9 | 50 | 0 | 0 | 4 |
| bis[N-(3-phenyl)prop-2-enyl) tropanium-3α-yl][1,10-decanedicarboxylate dibromide | 170 | 1.60 | 6.4 | 27 | 0 | -10 | 4 |

TABLE 6

| Monkey | ED50 | Onset | RI | VB | ΔHR | ΔBP | No |
|---|---|---|---|---|---|---|---|
| New Compounds: | | | | | | | |
| bis[N-(4-acetoxy-3-methoxybenzyl) quinuclidinium-3-yl] trans-3,6-endomethylene-1,2,3,6-tetrahydrophthalate dibromide | | | | | | | |
| bis[N-(2,5-dimethoxybenzyl) tropanium-3α-yl] trans-3,6-endomethylene-1,2,3,6-tetrahydrophthalate dibromide | | | | | | | |
| bis[N-(3,4,5-trimethoxybenzyl) tropanium-3α-yl] 1,9-nonanedicarboxylate dibromide | | | | | | | |
| bis[N-(4-acetoxy-3,5-dimethoxybenzyl) tropanium-3α-yl] 1,9-nonanedicarboxylate dibromide | | | | | | | |
| bis[N-(4-acetoxy-3,5-dimethoxybenzyl) tropanium-3α-yl] trans-3,6-endomethylene-1,2,3,6-tetrahydrophthalate dibromide | | | | | | | |
| bis[N-(4-acetoxy-3,5-dimethoxybenzyl) tropanium-3α-yl] cyclobutane-1,2-dicarboxylate dibromide | | | | | | | |
| bis[N-(3,5-dimethoxy-4-propionyloxybenzyl) tropanium-3α-yl] cyclohexane-1,3-dicarboxylate dibromide | | | | | | | |
| bis[N-(4-acetoxy-3-methoxybenzyl) tropanium-3α-yl] trans-3,6-endomethylene-1,2,3,6-tetrahydrophthalate dibromide | 55 | 0.85 | 0.5 | | 0 | 0 | 1 |
| bis[N-(4-acetoxy-3-methoxybenzyl) tropanium-3α-yl] cyclobutane-1,2-dicarboxylate dibromide | 92 | 0.75 | 0.5 | | 0 | 0 | 2 |
| bis[N-(4-acetoxy-3-methoxybenzyl) tropanium-3α-yl] cyclohexane-1,3-dicarboxylate dibromide | 100 | 0.9 | 0.5 | | 0 | 0 | 1 |
| bis[N-(3,4-diacetoxybenzyl) tropanium-3α-yl] trans-3,6-endomethylene-1,2,3,6-tetrahydrophthalate dibromide | 60 | 0.8 | 0.65 | | 0 | 0 | 2 |
| bis[N-(3,4-diacetoxybenzyl) tropanium-3α-yl] cyclobutane-1,2-dicarboxylate dibromide | 54 | 0.95 | 0.4 | | 0 | 0 | 3 |
| bis[N-(3,4-diacetoxybenzyl) tropanium-3α-yl] cyclohexane-1,3-dicarboxylate dibromide | 75 | 0.95 | 0.65 | | 0 | 0 | 2 |
| bis[N-(3,4-diacetoxybenzyl) tropanium-3β-yl] glutarate dibromide | 88 | 1 | 0.8 | | 0 | 0 | 3 |
| bis[N-(3,4-diacetoxybenzyl) tropanium-3β-yl] trans-3,6-endomethylene-1,2,3,6-tetrahydrophthalate dibromide | 75 | 0.7 | 0.4 | | 0 | 0 | 1 |
| bis[N-(3,4-diacetoxybenzyl) granataninium-3-yl] glutarate dibromide | 85 | 0.8 | 0.4 | | 0 | 0 | 3 |
| bis[N-(3,4-diacetoxybenzyl) granataninium-3-yl] adipate dibromide | 150 | 1.2 | 0.55 | | 0 | 0 | 1 |
| bis[N-(3,4-diacetoxybenzyl) granataninium-3-yl] pimelate dibromide | 200 | 0.9 | 0.4 | | 0 | 0 | 1 |
| bis[N-(3,4-diacetoxybenzyl) granataninium-3-yl] suberate dibromide | 86 | 0.7 | 0.4 | | 0 | 0 | 4 |
| bis[N-(3,4-diacetoxybenzyl) granataninium-3-yl] cyclobutane-1,2-dicarboxylate dibromide | | | | | | | |
| bis[N-(3,4-dipropionyloxybenzyl) tropanium-3α-yl] glutarate dibromide | | | | | | | |
| bis[N-(3,4-dipropionyloxybenzyl) tropanium-3α-yl] adipate dibromide | | | | | | | |
| bis[N-(3,4-dipropionyloxybenzyl) tropanium-3α-yl] cyclobutane-1,2-dicarboxylate dibromide | | | | | | | |
| bis[N-(3,4-dipropionyloxybenzyl) granataninium-3-yl] glutarate dibromide | | | | | | | |
| bis[N-(3,4-dipropionyloxybenzyl) granataninium-3-yl] adipate dibromide | | | | | | | |
| bis[N-(3,4-dipropionyloxybenzyl) granataninium-3-yl] pimelate dibromide | | | | | | | |
| bis[N-(3,4-dipropionyloxybenzyl) granataninium-3-yl] cyclobutane-1,2-dicarboxylate dibromide | | | | | | | |
| Comparison Compounds: | | | | | | | |
| Rocuronium | 13 | 3.5 | 5.6 | | 0 | 0 | 6 |
| Mivacurium | 34 | 1.9 | 2.4 | | 0 | 0 | 3 |
| Atracurium | 186 | 3 | 7.5 | | 0 | 0 | 6 |

TABLE 7

| Rabbit | ED50 | Onset | RI | VB | ΔHR | ΔBP | No |
|---|---|---|---|---|---|---|---|
| New Compounds: | | | | | | | |
| bis[N-(4-acetoxy-3-methoxybenzyl) quinuclidinium-3-yl] trans-3,6-endomethylene-1,2,3,6-tetrahydrophthalate dibromide | 115 | 2.8 | 4.5 | | 0 | 0 | 2 |
| bis[N-(2,5-dimethoxybenzyl) tropanium-3α-yl] trans-3,6-endomethylene-1,2,3,6-tetrahydrophthalate dibromide | 10 | 4 | 9 | | 0 | 0 | 2 |
| bis[N-(3,4,5-trimethoxybenzyl) tropanium-3α-yl] 1,9-nonanedicarboxylate dibromide | 70 | 1.3 | 2.5 | | 0 | 0 | 3 |
| bis[N-(4-acetoxy-3,5-dimethoxybenzyl) tropanium-3α-yl] trans-3,6-endomethylene-1,2,3,6-tetrahydrophthalate dibromide | 500 | 0.35 | 0.35 | | 0 | 0 | 3 |
| bis[N-(4-acetoxy-3,5-dimethoxybenzyl) tropanium-3α-yl] 1,9-nonanedicarboxylate dibromide | 145 | 0.45 | 0.45 | | 0 | 0 | 4 |
| bis[N-(4-acetoxy-3,5-dimethoxybenzyl) tropanium-3α-yl] cyclobutane-1,2-dicarboxylate dibromide | 298 | 0.5 | 0.55 | | 0 | 0 | 6 |
| bis[N-(3,5-dimethoxy-4-propionyloxybenzyl) tropanium-3α-yl] cyclohexane-1,3-dicarboxylate dibromide | 400 | 0.45 | 0.4 | | 0 | 0 | 3 |
| bis[N-(4-acetoxy-3-methoxybenzyl) tropanium-3α-yl] trans-3,6-endomethylene-1,2,3,6-tetrahydrophthalate dibromide | 155 | 0.65 | 0.65 | | 0 | 0 | 8 |
| bis[N-(4-acetoxy-3-methoxybenzyl) tropanium-3α-yl] cyclobutane-1,2-dicarboxylate dibromide | 75 | 0.6 | 0.55 | | 0 | 0 | 4 |
| bis[N-(4-acetoxy-3-methoxybenzyl) tropanium-3α-yl] cyclohexane-1,3-dicarboxylate dibromide | 165 | 0.65 | 0.65 | | 0 | 0 | 7 |
| bis[N-(3,4-diacetoxybenzyl) tropanium-3α-yl] trans-3,6-endomethylene-1,2,3,6-tetrahydrophthalate dibromide | 96 | 0.8 | 0.7 | | 0 | 0 | 5 |
| bis[N-(3,4-diacetoxybenzyl) tropanium-3α-yl] cyclobutane-1,2-dicarboxylate dibromide | 78 | 0.8 | 0.6 | | 0 | 0 | 4 |
| bis[N-(3,4-diacetoxybenzyl) tropanium-3α-yl] cyclohexane-1,3-dicarboxylate dibromide | 100 | 0.9 | 0.7 | | 0 | 0 | 4 |
| bis[N-(3,4-diacetoxybenzyl) tropanium-3α-yl] glutarate dibromide | 65 | 0.9 | 0.7 | | 0 | 0 | 6 |
| bis[N-(3,4-diacetoxybenzyl) tropanium-3β-yl] trans-3,6-endomethylene-1,2,3,6-tetrahydrophthalate dibromide | 210 | 0.8 | 0.75 | | 0 | 0 | 3 |
| bis[N-(3,4-diacetoxybenzyl) granataninium-3-yl] trans-3,6-endomethylene-1,2,3,6-tetrahydrophthalate dibromide | 165 | 0.65 | 0.55 | | 0 | 0 | 7 |
| bis[N-(3,4-diacetoxybenzyl) granataninium-3-yl] glutarate dibromide | 167 | 0.68 | 0.5 | | 0 | 0 | 3 |
| bis[N-(3,4-diacetoxybenzyl) granataninium-3-yl] adipate dibromide | 266 | 0.72 | 0.6 | | 0 | 0 | 4 |
| bis[N-(3,4-diacetoxybenzyl) granataninium-3-yl] pimelate dibromide | 475 | 0.4 | 0.55 | | 0 | 0 | 2 |
| bis[N-(3,4-diacetoxybenzyl) granataninium-3-yl] suberate dibromide | 115 | 0.6 | 0.6 | | 0 | 0 | 2 |
| bis[N-(3,4-diacetoxybenzyl) granataninium-3-yl] cyclobutane-1,2-dicarboxylate dibromide | 65 | 1 | 0.8 | | 0 | 0 | 3 |
| bis[N-(3,4-dipropionyloxybenzyl) tropanium-3α-yl] glutarate dibromide | 75 | 0.9 | 0.65 | | 0 | 0 | 3 |
| bis[N-(3,4-dipropionyloxybenzyl) tropanium-3α-yl] adipate dibromide | 128 | 0.87 | 0.5 | | 0 | 0 | 4 |
| bis[N-(3,4-dipropionyloxybenzyl) tropanium-3α-yl] cyclobutane-1,2-dicarboxylate dibromide | 135 | 0.7 | 0.55 | | 0 | 0 | 4 |
| bis[N-(3,4-dipropionyloxybenzyl) granataninium-3-yl] glutarate dibromide | 160 | 0.5 | 0.5 | | 0 | 0 | 2 |
| bis[N-(3,4-dipropionyloxybenzyl) granataninium-3-yl] adipate dibromide | 500 | 0.45 | 0.4 | | 0 | 0 | 2 |
| bis[N-(3,4-dipropionyloxybenzyl) granataninium-3-yl] pimelate dibromide | 225 | 0.55 | 0.5 | | 0 | 0 | 6 |
| bis[N-(3,4-dipropionyloxybenzyl) granataninium-3-yl] cyclobutane-1,2-dicarboxylate dibromide | | | | | | | |
| Comparison Compounds: | | | | | | | |
| Rocuronium | 30 | 1.1 | 2.4 | | 0 | 0 | 7 |
| Mivacurium | 20 | 2.8 | 3.9 | | 0 | 0 | 4 |
| Atracurium | 30 | 2.7 | 5.7 | | 0 | 0 | 7 |
| bis[N-benzyl tropanium-3α-yl] sebacate dibromide | 75 | 2.3 | 6 | | 0 | 0 | 2 |
| bis[N-ethyl tropanium-3α-yl] adipate diiodide | 150 | 2.2 | 9 | | 0 | 0 | 2 |

TABLE 8

| Dog | ED50 | Onset | RI | VB | ΔHR | ΔBP | No |
|---|---|---|---|---|---|---|---|
| New Compounds: | | | | | | | |
| bis[N-(4-acetoxy-3-methoxybenzyl) quinuclidinium-3-yl] trans-3,6-endomethylene-1,2,3,6-tetrahydrophthalate dibromide | | | | | | | |
| bis[N-(2,5-dimethoxybenzyl) tropanium-3α-yl] trans-3,6-endomethylene-1,2,3,6-tetrahydrophthalate dibromide | | | | | | | |
| bis[N-(3,4,5-trimethoxybenzyl) tropanium-3α-yl] 1,9-nonanedicarboxylate dibromide | | | | | | | |
| bis[N-(4-acetoxy-3,5-dimethoxybenzyl) tropanium-3α-yl] 1,9-nonanedicarboxylate dibromide | | | | | | | |
| bis[N-(4-acetoxy-3,5-dimethoxybenzyl) tropanium-3α-yl] trans-3,6-endomethylene-1,2,3,6-tetrahydrophthalate dibromide | | | | | | | |
| bis[N-(4-acetoxy-3,5-dimethoxybenzyl) tropanium-3α-yl] cyclobutane-1,2-dicarboxylate dibromide | | | | | | | |
| bis[N-(3,5-dimethoxy-4-propionyloxybenzyl) tropanium-3α-yl] cyclohexane-1,3-dicarboxylate dibromide | | | | | | | |
| bis[N-(4-acetoxy-3-methoxybenzyl) tropanium-3α-yl] trans-3,6-endomethylene-1,2,3,6-tetrahydrophthalate dibromide | 350 | 0.63 | 0.5 | | 40 | −25 | 2 |
| bis[N-(4-acetoxy-3-methoxybenzyl) tropanium-3α-yl] cyclobutane-1,2-dicarboxylate dibromide | 145 | 0.85 | 0.7 | | 45 | −15 | 2 |
| bis[N-(4-acetoxy-3-methoxybenzyl) tropanium-3α-yl] cyclohexane-1,3-dicarboxylate dibromide | 280 | 0.75 | 0.5 | | 38 | −25 | 4 |
| bis[N-(3,4-diacetoxybenzyl) tropanium-3α-yl] trans-3,6-endomethylene-1,2,3,6-tetrahydrophthalate dibromide | | | | | | | |
| bis[N-(3,4-diacetoxybenzyl) tropanium-3α-yl] cyclobutane-1,2-dicarboxylate dibromide | 100 | 0.9 | 0.65 | | 10 | −7 | 5 |
| bis[N-(3,4-diacetoxybenzyl) tropanium-3α-yl] cyclohexane-1,3-dicarboxylate dibromide | 128 | 0.75 | 0.55 | | 30 | −5 | 4 |
| bis[N-(3,4-diacetoxybenzyl) tropanium-3α-yl] glutarate dibromide | 110 | 0.9 | 0.6 | | 0 | 0 | 5 |
| bis[N-(3,4-diacetoxybenzyl) tropanium-3β-yl] trans-3,6-endomethylene-1,2,3,6-tetrahydrophthalate dibromide | 225 | 0.65 | 0.6 | | 50 | −18 | 2 |
| bis[N-(3,4-diacetoxybenzyl) granataninium-3-yl] glutarate dibromide | | | | | | | |
| bis[N-(3,4-diacetoxybenzyl) granataninium-3-yl] adipate dibromide | | | | | | | |
| bis[N-(3,4-diacetoxybenzyl) granataninium-3-yl] pimelate dibromide | | | | | | | |
| bis[N-(3,4-diacetoxybenzyl) granataninium-3-yl] suberate dibromide | 250 | 0.8 | 0.45 | | 60 | −55 | 2 |
| bis[N-(3,4-diacetoxybenzyl) granataninium-3-yl] cyclobutane-1,2-dicarboxylate dibromide | 150 | 0.75 | 0.7 | | 27 | −5 | 4 |
| bis[N-(3,4-dipropionyloxybenzyl) tropanium-3α-yl] glutarate dibromide | | | | | | | |
| bis[N-(3,4-dipropionyloxybenzyl) tropanium-3α-yl] adipate dibromide | | | | | | | |
| bis[N-(3,4-dipropionyloxybenzyl) tropanium-3α-yl] cyclobutane-1,2-dicarboxylate dibromide | | | | | | | |
| bis[N-(3,4-dipropionyloxybenzyl) granataninium-3-yl] glutarate dibromide | | | | | | | |
| bis[N-(3,4-dipropionyloxybenzyl) granataninium-3-yl] adipate dibromide | | | | | | | |
| bis[N-(3,4-dipropionyloxybenzyl) granataninium-3-yl] pimelate dibromide | | | | | | | |
| bis[N-(3,4-dipropionyloxybenzyl) granataninium-3-yl] cyclobutane-1,2-dicarboxylate dibromide | | | | | | | |
| Comparison Compounds: | | | | | | | |
| Rocuronium | 76 | 1.9 | 3.3 | | 0 | 0 | 3 |

What is claimed is:

1. A process for preparing a compound of the formula

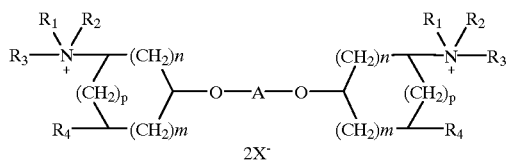

where $R_1$ is di- or polysubstituted aralkyl or aralkenyl; $R_2$ is alkyl or alkenyl; provided that at least one substituent on each aralkyl or aralkenyl group is alkoxy or acyloxy; A is normal or substituted alkanedicarbonyl, alkenedicarbonyl, alkynedicarbonyl, cycloalkanedicarbonyl, cycloalkenedicarbonyl, bicycloalkanedicarbonyl, bicycloalkenedicarbonyl, polycycloalkanedicarbonyl, or aromatic dicarbonyl; n is 0, 1, or 2; m is 0, 1, or 2; p is 0, 1, or 2; $R_3$ is H, $CH_3$, or lower alkyl; $R_4$ is H, $CH_3$, or lower alkyl; $R_3$ and $R_4$ together can also be $-(CH_2)_g-$, $-CH=CH-$, $-(CH_2)_h-O-(CH_2)_k-$, or $-(CH_2)_h-S-(CH_2)_k-$, where g is 2, 3, 4, or 5, h is 1 or 2, and k is 1 or 2; and X is a pharmaceutically acceptable anion;

which comprises reacting a compound of the formula

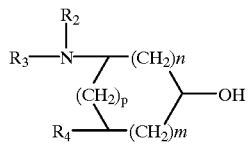

with a compound of the formula

to produce a first reaction product of the formula

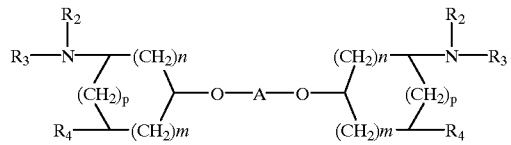

and reacting said first reaction product with a compound of the formula

to produce a second reaction product of the formula

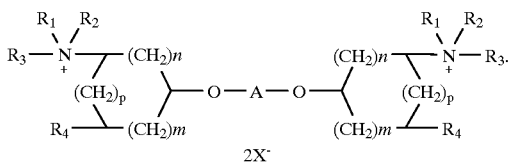

2. A process for preparing a compound of the formula

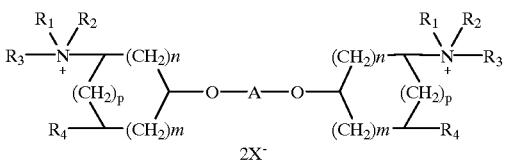

where $R_1$ is di- or polysubstituted aralkyl or aralkenyl; $R_2$ is alkyl or alkenyl; provided that at least one substituent on each aralkyl or aralkenyl group is alkoxy or acyloxy; A is normal or substituted alkanedicarbonyl, alkenedicarbonyl, alkynedicarbonyl, cycloalkanedicarbonyl, cycloalkenedicarbonyl, bicycloalkanedicarbonyl, bicycloalkenedicarbonyl, polycycloalkanedicarbonyl, or aromatic dicarbonyl; n is 0, 1, or 2; m is 0, 1, or 2; $R_3$ is H, $CH_3$, or lower alkyl; $R_4$ is H, $CH_3$, or lower alkyl; $R_3$ and $R_4$ together can also be $-(CH_2)_g-$, $-CH=CH-$, $-(CH_2)_h-O-(CH_2)_k-$, or $-(CH_2)_h-S-(CH_2)_k-$, where g is 2, 3, 4, or 5, h is 1 or 2, and k is 1 or 2; and X is a pharmaceutically acceptable anion;

which comprises reacting a compound of the formula

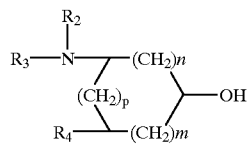

with a compound of the formula

to produce a first reaction product of the formula

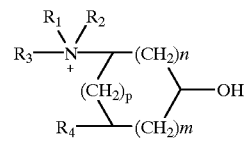

and reacting said first reaction product with a compound of the formula

to produce a second reaction product of the formula

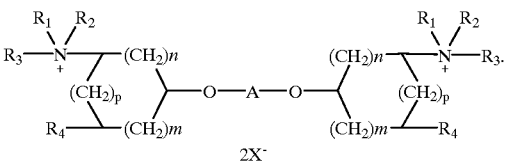

3. A process for preparing a compound of the formula

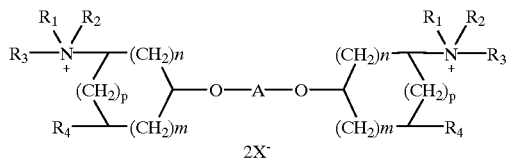

where $R_1$ is di- or polysubstituted aralkyl or aralkenyl; provided that at least one substituent on each aralkyl or aralkenyl group is alkoxy or acyloxy; A is normal or substituted alkanedicarbonyl, alkenedicarbonyl, alkynedicarbonyl, cycloalkanedicarbonyl, cycloalkenedicarbonyl, bicycloalkanedicarbonyl, bicycloalkenedicarbonyl, polycycloalkanedicarbonyl, or aromatic dicarbonyl; n is 0, 1, or 2; m is 0, 1, or 2; p is 0, 1, or 2; $R_3$ is H, $CH_3$, or lower alkyl; $R_4$ is H, $CH_3$, or lower alkyl; $R_3$ and $R_4$ together can also be $-(CH_2)_g-$, $-CH=CH-$, $-(CH_2)_h-O-(CH_2)_k-$, or $-(CH_2)_h-S-(CH_2)_k-$, where g is 2, 3, 4, or 5, h is 1 or 2, and k is 1 or 2; and X is a pharmaceutically acceptable anion; which comprises reacting a compound of the formula

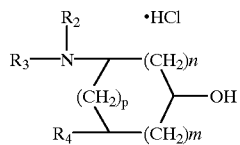

with a compound of the formula

to produce a first reaction product of the formula

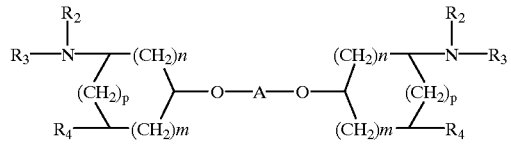

and reacting said first reaction product with a compound of the formula

to produce a second reaction product of the formula

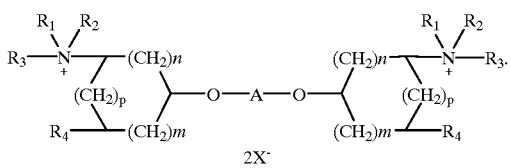

4. A process for preparation of a compound of the formula

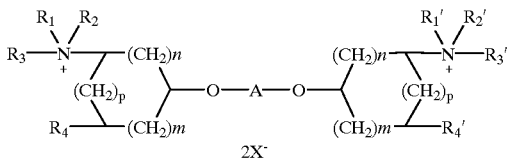

where $R_1$ and $R_1'$ are di- or polysubstituted aralkyl or aralkenyl; $R_2$ and $R_2'$ are alkyl or alkenyl; provided that at least one substituent on each aralkyl or aralkenyl group is alkoxy or acyloxy; A is normal or substituted alkanedicarbonyl, alkenedicarbonyl, alkynedicarbonyl, cycloalkanedicarbonyl, cycloalkenedicarbonyl, bicycloalkanedicarbonyl, bicycloalkenedicarbonyl, polycycloalkanedicarbonyl, or aromatic dicarbonyl; n is 0, 1, or 2; m is 0, 1, or 2; p is 0, 1, or 2; $R_3$ and $R_3'$ are H, $CH_3$, or lower alkyl; $R_4$ and $R_4'$ are H, $CH_3$, or lower alkyl; $R_3$ and $R_4$ together can also be $-(CH_2)_g-$, $-CH=CH-$, $-(CH_2)_h-O-(CH_2)_k-$, or $-(CH_2)_h-S-(CH_2)_k-$, where g is 2, 3, 4, or 5, h is 1 or 2, and k is 1 or 2 and $R_3'$ and $R_4'$ together can also be $-(CH_2)_g-$, $-CH=CH-$, $-(CH_2)_h-O-(CH_2)_k-$, or $-(CH_2)_h-S-(CH_2)_k-$, where g is 2, 3, 4, or 5, h is 1 or 2, and k is 1 or 2; where $R_1$ and $R_1'$, $R_2$ and $R_2'$, $R_3$ and $R_3'$, and $R_4$ and $R_4'$ can be the same or different; and X is a pharmaceutically acceptable anion; which comprises reacting a compound of the formula

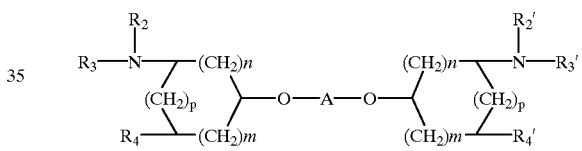

with about one equivalent of a compound of the formula

and then reacting the resulting first reaction product with about one equivalent of a compound of the formula

to produce a second reaction product of the formula

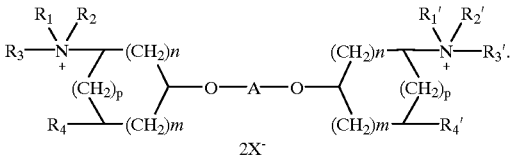

* * * * *